US012440371B2

(12) United States Patent
Franklin et al.

(10) Patent No.: US 12,440,371 B2
(45) Date of Patent: Oct. 14, 2025

(54) FLUID COLLECTION SYSTEM INCLUDING A GARMENT AND A FLUID COLLECTION DEVICE

(71) Applicant: PUREWICK CORPORATION, Covington, GA (US)

(72) Inventors: Jeff Edward Franklin, Hamilton, OH (US); Brandt Davis, Milford, OH (US); Michael Lambert, Snellville, GA (US); Kevin Michael Knollman, West Chester, OH (US); Kyra Kormos Wesner, Loveland, OH (US); Michelle Schnell, Hamilton, OH (US); Mackenzie Brooke Weir, Chardon, OH (US); Joseph Andrew Filbrun, Cincinatti, OH (US)

(73) Assignee: PUREWICK CORPORATION, Covington, GA (US)

( * ) Notice: Subject to any disclaimer, the term of this patent is extended or adjusted under 35 U.S.C. 154(b) by 447 days.

(21) Appl. No.: 18/007,105

(22) PCT Filed: Aug. 5, 2021

(86) PCT No.: PCT/US2021/044699
§ 371 (c)(1),
(2) Date: Jan. 27, 2023

(87) PCT Pub. No.: WO2022/031943
PCT Pub. Date: Feb. 10, 2022

(65) Prior Publication Data

US 2023/0225898 A1 Jul. 20, 2023

Related U.S. Application Data

(60) Provisional application No. 63/061,834, filed on Aug. 6, 2020.

(51) Int. Cl.
*A61F 5/455* (2006.01)
*A61F 5/44* (2006.01)
*A61F 5/453* (2006.01)

(52) U.S. Cl.
CPC .............. *A61F 5/455* (2013.01); *A61F 5/453* (2013.01)

(58) Field of Classification Search
CPC ...... A61F 5/451; A61F 5/4401; A61F 5/4408; A61F 5/443
See application file for complete search history.

(56) References Cited

U.S. PATENT DOCUMENTS 670,602 A 3/1901 Baker
737,443 A 8/1903 Mooers
(Continued)

FOREIGN PATENT DOCUMENTS

AU 2018216821 A1 8/2019
AU 2021299304 A1 2/2023
(Continued)

OTHER PUBLICATIONS

US 9,908,683 B2, 03/2018, Sandhausen et al. (withdrawn)
(Continued)

*Primary Examiner* — Guy K Townsend
(74) *Attorney, Agent, or Firm* — Ballard Spahr LLP

(57) ABSTRACT

Example fluid collection systems and methods of use are described. The fluid collection system includes a garment and a fluid collection device. The garment is configured to be worn on a pelvis of a user, and includes at least a crotch portion having an inner surface and at least one of a strap partially defining a through hole between the strap and the inner surface or a pocket on the inner surface of the crotch portion. The at least one of the strap or the pocket are positioned on the crotch portion of the garment and the fluid
(Continued)

collection device is sized to position the opening and the fluid permeable body proximate to a urethra of the user.

31 Claims, 11 Drawing Sheets

(56) References Cited

U.S. PATENT DOCUMENTS 1,015,905 A 1/1912 Northrop
1,032,841 A 7/1912 Koenig
1,178,644 A 4/1916 Johnson
1,387,726 A 8/1921 Karge
1,742,080 A 12/1929 Jones
1,979,899 A 11/1934 Obrien et al.
2,241,010 A 5/1941 Chipley
2,262,772 A 11/1941 Peder
2,326,881 A 8/1943 Packer
2,379,346 A 6/1945 Farrell
2,485,555 A 10/1949 Bester
2,571,357 A 10/1951 Charles
2,613,670 A 10/1952 Edward
2,616,426 A 11/1952 Adele
2,644,234 A 7/1953 Earl
2,648,335 A 8/1953 Chambers
2,859,786 A 11/1958 Tupper
2,944,551 A 7/1960 Carl
2,968,046 A * 1/1961 Duke ..................... A61G 9/006 604/149
2,971,512 A 2/1961 Reinhardt
3,032,038 A 5/1962 Swinn
3,077,883 A 2/1963 Hill
3,087,938 A 4/1963 Hans et al.
3,169,528 A 2/1965 Knox et al.
3,171,506 A 3/1965 Therkel
3,194,238 A 7/1965 Breece
3,198,994 A 8/1965 Hildebrandt et al.
3,221,742 A 12/1965 Egon
3,312,221 A 4/1967 Overment
3,312,981 A 4/1967 McGuire et al.
3,349,768 A 10/1967 Keane
3,362,590 A 1/1968 Gene
3,366,116 A 1/1968 Huck
3,398,848 A 8/1968 Donovan
3,400,717 A 9/1968 Bruce et al.
3,406,688 A 10/1968 Bruce
3,424,163 A 1/1969 Gravdahl
3,425,471 A 2/1969 Yates
3,511,241 A 5/1970 Lee
3,512,185 A 5/1970 Ellis
3,520,300 A 7/1970 Flower
3,528,423 A 9/1970 Lee
3,613,123 A 10/1971 Langstrom
3,648,700 A 3/1972 Warner
3,651,810 A 3/1972 Ormerod
3,661,155 A 5/1972 Lindan
3,683,918 A 8/1972 Pizzella
3,699,815 A 10/1972 Holbrook
3,726,277 A 4/1973 Hirschman
3,742,952 A 7/1973 Magers et al.
3,757,355 A 9/1973 Allen et al.
3,788,324 A 1/1974 Lim
3,843,016 A 10/1974 Bornhorst et al.
3,863,638 A 2/1975 Rogers et al.
3,863,798 A 2/1975 Kurihara et al.
3,864,759 A 2/1975 Horiuchi
3,865,109 A 2/1975 Elmore et al.
3,881,486 A 5/1975 Fenton
3,881,489 A 5/1975 Hartwell
3,915,189 A 10/1975 Holbrook et al.
3,998,228 A 12/1976 Poidomani
3,999,550 A 12/1976 Martin
4,015,604 A 4/1977 Csillag
4,020,843 A 5/1977 Kanall
4,022,213 A 5/1977 Stein
4,027,776 A 6/1977 Douglas
4,064,962 A 12/1977 Hunt
4,116,197 A 9/1978 Bermingham
4,180,178 A 12/1979 Turner
4,187,953 A 2/1980 Turner
4,194,508 A 3/1980 Anderson
4,200,102 A * 4/1980 Duhamel ................ A61F 5/451 604/353
4,202,058 A 5/1980 Anderson
4,203,503 A 5/1980 Bertotti et al.
4,209,076 A 6/1980 Bertotti et al.
4,223,677 A 9/1980 Anderson
4,233,025 A 11/1980 Larson et al.
4,233,978 A 11/1980 Hickey
4,246,901 A 1/1981 Frosch et al.
4,253,542 A 3/1981 Ruspa et al.
4,257,418 A 3/1981 Hessner
4,270,539 A 6/1981 Frosch et al.
4,281,655 A 8/1981 Terauchi
4,292,916 A 10/1981 Bradley et al.
4,330,239 A 5/1982 Gannaway
4,352,356 A 10/1982 Tong
4,360,933 A 11/1982 Kimura et al.
4,365,363 A 12/1982 Windauer
4,375,841 A 3/1983 Vielbig
4,387,726 A 6/1983 Denard
4,403,991 A 9/1983 Hill
4,425,130 A 1/1984 Desmarais
4,446,986 A 5/1984 Bowen et al.
4,453,938 A 6/1984 Brendling
4,457,314 A 7/1984 Knowles
4,476,879 A 10/1984 Jackson
4,526,688 A 7/1985 Schmidt et al.
4,528,703 A 7/1985 Kraus
D280,438 S 9/1985 Wendt
4,551,141 A 11/1985 Mcneil
4,553,968 A 11/1985 Komis
4,581,026 A 4/1986 Schneider
4,589,516 A 5/1986 Inoue et al.
4,601,716 A 7/1986 Smith
4,610,675 A 9/1986 Triunfol
4,620,333 A 11/1986 Ritter
4,626,250 A 12/1986 Schneider
4,627,846 A 12/1986 Ternstroem
4,631,061 A 12/1986 Martin
4,650,477 A 3/1987 Johnson
4,655,754 A 4/1987 Richmond et al.
4,656,675 A 4/1987 Fajnsztajn
4,681,570 A 7/1987 Dalton
4,681,577 A 7/1987 Stern et al.
4,692,160 A 9/1987 Nussbaumer
4,707,864 A 11/1987 Ikematsu et al.
4,713,065 A 12/1987 Koot
4,713,066 A 12/1987 Komis
4,723,953 A 2/1988 Pratt et al.
4,735,841 A 4/1988 Sourdet
4,743,236 A 5/1988 Manschot
4,747,166 A * 5/1988 Kuntz ..................... A61F 5/455 4/144.1
4,752,944 A 6/1988 Conrads et al.
4,769,215 A 9/1988 Ehrenkranz
4,771,484 A 9/1988 Mozell
4,772,280 A 9/1988 Rooyakkers
4,784,654 A 11/1988 Beecher
4,790,830 A 12/1988 Hamacher
4,790,835 A 12/1988 Elias
4,791,686 A 12/1988 Taniguchi et al.
4,795,449 A * 1/1989 Schneider ............... A61F 5/441 604/326
4,798,603 A 1/1989 Meyer et al.
4,799,928 A 1/1989 Crowley
4,804,377 A 2/1989 Hanifl et al.
4,812,053 A 3/1989 Bhattacharjee
4,813,943 A 3/1989 Smith
4,820,297 A 4/1989 Kaufman et al.
4,846,818 A 7/1989 Keldahl et al.
4,846,909 A 7/1989 Klug et al.
4,865,595 A 9/1989 Heyden
4,880,417 A 11/1989 Yabrov et al.
4,882,794 A 11/1989 Stewart

(56) References Cited

U.S. PATENT DOCUMENTS 4,883,465 A 11/1989 Brennan
4,886,498 A 12/1989 Newton
4,886,508 A * 12/1989 Washington ............ A61F 5/455 604/347
4,886,509 A 12/1989 Mattsson
4,889,532 A 12/1989 Metz et al.
4,889,533 A 12/1989 Beecher
4,890,691 A 1/1990 Ching-ho
4,903,254 A 2/1990 Haas
4,904,248 A 2/1990 Vaillancourt
4,905,692 A 3/1990 More
4,936,838 A 6/1990 Cross et al.
4,955,922 A 9/1990 Terauchi
4,957,487 A 9/1990 Gerow
4,965,460 A 10/1990 Tanaka et al.
4,986,823 A 1/1991 Anderson et al.
4,987,849 A 1/1991 Sherman
5,002,541 A 3/1991 Conkling et al.
5,004,463 A 4/1991 Nigay
5,031,248 A 7/1991 Kemper
5,045,077 A 9/1991 Blake
5,045,283 A 9/1991 Patel
5,049,144 A 9/1991 Payton
5,053,339 A 10/1991 Patel
5,057,092 A 10/1991 Webster
5,058,088 A 10/1991 Haas et al.
5,071,347 A 12/1991 McGuire
5,078,707 A 1/1992 Peter
5,084,037 A 1/1992 Barnett
5,100,396 A 3/1992 Zamierowski
5,112,324 A 5/1992 Wallace
5,147,301 A 9/1992 Ruvio
5,176,667 A 1/1993 Debring
5,195,997 A 3/1993 Carns
5,196,654 A 3/1993 Diflora et al.
5,203,699 A 4/1993 McGuire
5,244,458 A 9/1993 Takasu
5,246,454 A 9/1993 Peterson
5,267,988 A 12/1993 Farkas
5,275,307 A 1/1994 Freese
5,282,795 A 2/1994 Finney
5,294,983 A 3/1994 Ersoz et al.
5,295,983 A 3/1994 Kubo
5,300,052 A 4/1994 Kubo
5,304,749 A 4/1994 Crandell
5,312,383 A 5/1994 Kubalak
5,318,550 A 6/1994 Cermak et al.
5,330,459 A 7/1994 Lavon et al.
5,340,840 A 8/1994 Park et al.
5,382,244 A 1/1995 Telang
5,409,014 A 4/1995 Napoli et al.
5,411,495 A 5/1995 Willingham
5,423,784 A 6/1995 Metz
5,456,246 A 10/1995 Schmieding et al.
5,466,229 A 11/1995 Elson et al.
5,478,334 A 12/1995 Bernstein
5,499,977 A 3/1996 Marx
5,543,042 A 8/1996 Filan et al.
D373,928 S 9/1996 Green
5,582,604 A 12/1996 Ahr et al.
5,592,950 A 1/1997 Kopelowicz
5,605,161 A 2/1997 Cross
5,618,277 A 4/1997 Goulter
5,628,735 A 5/1997 Skow
5,636,643 A 6/1997 Argenta et al.
5,637,104 A 6/1997 Ball et al.
5,674,212 A 10/1997 Osborn et al.
5,678,564 A 10/1997 Lawrence et al.
5,678,654 A 10/1997 Uzawa
5,687,429 A 11/1997 Rahlff
5,695,485 A 12/1997 Duperret et al.
5,700,254 A 12/1997 Mcdowall et al.
5,701,612 A 12/1997 Daneshvar
5,705,777 A 1/1998 Flanigan et al.
5,752,944 A 5/1998 Dann et al.
5,763,333 A 6/1998 Suzuki et al.
5,772,644 A 6/1998 Bark et al.
5,792,132 A 8/1998 Garcia
5,827,243 A 10/1998 Palestrant
5,827,247 A 10/1998 Kay
5,827,250 A 10/1998 Fujioka et al.
5,827,257 A 10/1998 Fujioka et al.
D401,699 S 11/1998 Herchenbach et al.
5,859,393 A 1/1999 Cummins et al.
5,865,378 A 2/1999 Hollinshead et al.
5,876,393 A 3/1999 Ahr et al.
5,887,291 A 3/1999 Bellizzi
5,891,125 A 4/1999 Plumley
5,894,608 A * 4/1999 Birbara ................ A61F 5/4556 604/319
D409,303 S 5/1999 Oepping
5,911,222 A 6/1999 Lawrence et al.
5,957,904 A 9/1999 Holland
5,968,026 A 10/1999 Osborn et al.
5,972,505 A 10/1999 Phillips et al.
6,007,526 A 12/1999 Passalaqua et al.
6,039,060 A 3/2000 Rower
6,050,983 A 4/2000 Moore et al.
6,059,762 A 5/2000 Boyer et al.
6,063,064 A 5/2000 Tuckey et al.
6,098,625 A 8/2000 Winkler
6,105,174 A 8/2000 Karlsten et al.
6,113,582 A 9/2000 Dwork
6,117,163 A 9/2000 Bierman
6,123,398 A * 9/2000 Arai .................... B60T 8/17552 303/151
6,129,718 A 10/2000 Wada et al.
6,131,964 A 10/2000 Sareshwala
6,152,902 A 11/2000 Christian et al.
6,164,569 A 12/2000 Hollinshead et al.
6,177,606 B1 1/2001 Etheredge et al.
6,209,142 B1 4/2001 Mattsson et al.
6,220,050 B1 4/2001 Cooksey
6,244,311 B1 6/2001 Hand et al.
6,248,096 B1 6/2001 Dwork et al.
6,263,887 B1 7/2001 Dunn
6,283,246 B1 9/2001 Nishikawa
6,311,339 B1 * 11/2001 Kraus ..................... A61F 5/451 4/144.1
6,336,919 B1 1/2002 Davis et al.
6,338,729 B1 1/2002 Wada et al.
6,352,525 B1 3/2002 Wakabayashi
6,394,988 B1 5/2002 Hashimoto
6,398,742 B1 6/2002 Kim
6,406,463 B1 6/2002 Brown
6,409,712 B1 6/2002 Dutari et al.
6,416,500 B1 7/2002 Wada et al.
6,423,045 B1 7/2002 Wise et al.
6,428,521 B1 8/2002 Droll
6,428,522 B1 8/2002 Dipalma et al.
6,446,454 B1 9/2002 Lee et al.
6,475,198 B1 11/2002 Lipman et al.
6,479,726 B1 11/2002 Cole et al.
6,491,673 B1 12/2002 Palumbo et al.
6,508,794 B1 1/2003 Palumbo et al.
6,524,292 B1 2/2003 Dipalma et al.
6,540,729 B1 4/2003 Wada et al.
6,547,771 B2 4/2003 Robertson et al.
6,569,133 B2 5/2003 Cheng et al.
D476,518 S 7/2003 Doppelt
6,592,560 B2 7/2003 Snyder et al.
6,610,038 B1 8/2003 Dipalma et al.
6,618,868 B2 9/2003 Minnick
6,620,142 B1 9/2003 Flueckiger
6,629,651 B1 10/2003 Male et al.
6,635,038 B2 10/2003 Scovel
6,652,495 B1 11/2003 Walker
6,666,850 B1 12/2003 Ahr et al.
6,685,684 B1 2/2004 Falconer
6,695,828 B1 2/2004 Dipalma et al.
6,699,174 B1 3/2004 Bennett
6,700,034 B1 3/2004 Lindsay et al.
6,702,793 B1 3/2004 Sweetser et al.

(56) References Cited

U.S. PATENT DOCUMENTS 6,706,027 B2 * 3/2004 Harvie .................... A61F 5/453 604/326
6,732,384 B2 * 5/2004 Scott ...................... A47K 11/12 4/144.1
6,736,977 B1 5/2004 Hall et al.
6,740,066 B2 * 5/2004 Wolff ...................... A61F 5/451 604/323
6,764,477 B1 7/2004 Chen et al.
6,783,519 B2 8/2004 Samuelsson
6,796,974 B2 9/2004 Palumbo et al.
6,814,547 B2 11/2004 Childers et al.
6,849,065 B2 2/2005 Schmidt et al.
6,857,137 B2 2/2005 Otto
6,885,690 B2 4/2005 Aggerstam et al.
6,888,044 B2 5/2005 Fell et al.
6,893,425 B2 5/2005 Dunn et al.
6,912,737 B2 7/2005 Ernest et al.
6,918,899 B2 * 7/2005 Harvie .................... A61F 5/451 604/326
6,979,324 B2 12/2005 Bybordi et al.
7,018,366 B2 * 3/2006 Easter ..................... A61F 5/451 604/327
7,066,411 B2 6/2006 Male et al.
7,122,023 B1 10/2006 Hinoki
7,125,399 B2 10/2006 Miskie
7,131,964 B2 * 11/2006 Harvie .................... A61F 5/455 604/326
7,135,012 B2 * 11/2006 Harvie .................... A61F 5/453 604/326
7,141,043 B2 * 11/2006 Harvie .................... A61F 5/451 604/326
D533,972 S 12/2006 La
7,160,273 B2 1/2007 Greter et al.
7,171,699 B2 2/2007 Ernest et al.
7,171,871 B2 2/2007 Kozak
7,179,951 B2 2/2007 Krishnaswamy-Mirle et al.
7,181,781 B1 * 2/2007 Trabold .................. A61F 5/455 4/144.1
7,186,245 B1 3/2007 Cheng et al.
7,192,424 B2 3/2007 Cooper
7,219,764 B1 5/2007 Forbes
7,220,250 B2 * 5/2007 Suzuki .................... A61F 5/451 604/328
D562,975 S 2/2008 Otto
7,335,189 B2 * 2/2008 Harvie .................... A61F 5/451 604/326
7,358,282 B2 4/2008 Krueger et al.
7,390,320 B2 * 6/2008 Machida ................. A61F 5/455 4/144.1
7,438,706 B2 10/2008 Koizumi et al.
7,488,310 B2 2/2009 Yang
7,491,194 B1 2/2009 Oliwa
D591,106 S 4/2009 Dominique et al.
7,513,381 B2 4/2009 Heng et al.
7,520,872 B2 4/2009 Biggie et al.
D593,801 S 6/2009 Wilson et al.
7,540,364 B2 6/2009 Sanderson
7,549,511 B2 6/2009 Marocco
7,549,512 B2 6/2009 Newberry
7,585,293 B2 9/2009 Vermaak
7,588,560 B1 9/2009 Dunlop
7,637,905 B2 12/2009 Saadat et al.
7,665,359 B2 2/2010 Barber
7,682,347 B2 3/2010 Parks et al.
7,687,004 B2 3/2010 Allen
7,695,459 B2 4/2010 Gilbert et al.
7,695,460 B2 4/2010 Wada et al.
7,699,818 B2 4/2010 Gilbert
7,699,831 B2 * 4/2010 Bengtson .............. A61M 27/00 604/313
7,722,584 B2 5/2010 Tanaka et al.
7,727,206 B2 6/2010 Gorres
7,740,620 B2 6/2010 Gilbert et al.
7,749,205 B2 * 7/2010 Tazoe ...................... A61F 5/451 604/320
7,755,497 B2 * 7/2010 Wada ...................... A61F 5/451 340/604
7,766,887 B2 8/2010 Burns et al.
D625,407 S 10/2010 Koizumi et al.
7,806,879 B2 10/2010 Brooks et al.
7,811,272 B2 10/2010 Lindsay et al.
7,815,067 B2 10/2010 Matsumoto et al.
7,833,169 B2 11/2010 Hannon
7,857,806 B2 12/2010 Karpowicz et al.
7,866,942 B2 1/2011 Harvie
7,871,385 B2 1/2011 Levinson et al.
7,875,010 B2 1/2011 Frazier et al.
7,901,389 B2 3/2011 Mombrinie
7,927,320 B2 4/2011 Goldwasser et al.
7,927,321 B2 4/2011 Marland
7,931,634 B2 4/2011 Swiecicki et al.
7,939,706 B2 5/2011 Okabe et al.
7,946,443 B2 5/2011 Stull et al.
7,947,025 B2 5/2011 Buglino et al.
7,963,419 B2 6/2011 Burney et al.
7,976,519 B2 7/2011 Bubb et al.
7,993,318 B2 8/2011 Olsson et al.
8,015,627 B2 9/2011 Baker et al.
8,016,071 B1 9/2011 Martinus et al.
8,028,460 B2 10/2011 Williams
8,047,398 B2 11/2011 Dimartino et al.
8,083,094 B2 12/2011 Caulfield et al.
8,128,608 B2 * 3/2012 Thevenin ................ A61F 13/84 604/347
8,181,651 B2 5/2012 Pinel
8,181,819 B2 5/2012 Burney et al.
8,211,063 B2 * 7/2012 Bierman ............... A61M 25/02 604/179
8,221,369 B2 7/2012 Parks et al.
8,241,262 B2 8/2012 Mahnensmith
8,277,426 B2 10/2012 Wilcox et al.
8,287,508 B1 * 10/2012 Sanchez ................ A61F 5/4404 604/326
8,303,554 B2 11/2012 Tsai et al.
8,322,565 B2 12/2012 Caulfield et al.
8,337,477 B2 12/2012 Parks et al.
D674,241 S 1/2013 Bickert et al.
8,343,122 B2 1/2013 Gorres
8,343,125 B2 1/2013 Kawazoe et al.
8,353,074 B2 1/2013 Krebs
8,353,886 B2 1/2013 Bester et al.
D676,241 S 2/2013 Merrill
8,388,588 B2 3/2013 Wada et al.
D679,807 S 4/2013 Burgess et al.
8,425,482 B2 4/2013 Khoubnazar
8,434,586 B2 5/2013 Pawelski et al.
8,449,510 B2 5/2013 Martini et al.
D684,260 S 6/2013 Lund et al.
8,470,230 B2 6/2013 Caulfield et al.
8,479,941 B2 7/2013 Matsumoto et al.
8,479,949 B2 7/2013 Henkel
8,500,719 B1 8/2013 Simpson et al.
8,512,301 B2 8/2013 Ma
8,529,530 B2 9/2013 Koch et al.
8,535,284 B2 9/2013 Joder et al.
8,546,639 B2 * 10/2013 Wada .................... A61F 5/4401 604/361
8,551,075 B2 * 10/2013 Bengtson ................ A61M 1/84 604/543
8,568,376 B2 * 10/2013 Delattre ................ A61F 13/471 604/385.01
D694,404 S 11/2013 Burgess et al.
8,585,683 B2 * 11/2013 Bengtson .............. A61M 1/985 604/543
8,586,583 B2 11/2013 Hamblin et al.
8,652,112 B2 2/2014 Johannison et al.
8,669,412 B2 3/2014 Fernkvist et al.
D702,973 S 4/2014 Norland et al.
8,703,032 B2 4/2014 Menon et al.
D704,330 S 5/2014 Cicatelli
D704,510 S 5/2014 Mason et al.

(56) References Cited

U.S. PATENT DOCUMENTS

D705,423 S 5/2014 Walsh Cutler
D705,926 S 5/2014 Burgess et al.
8,714,394 B2 5/2014 Wulf
8,715,267 B2 5/2014 Bengtson et al.
8,757,425 B2 6/2014 Copeland
8,777,032 B2 7/2014 Biesecker et al.
8,808,260 B2 8/2014 Koch et al.
8,864,730 B2 * 10/2014 Conway ................ A61F 5/4401 604/346
8,881,923 B2 11/2014 Higginson
8,882,731 B2 * 11/2014 Suzuki .................... A61F 5/451 604/327
8,936,585 B2 1/2015 Carson et al.
D729,581 S 5/2015 Boroski
9,028,460 B2 * 5/2015 Medeiros ................ A61F 5/451 604/347
9,056,698 B2 6/2015 Noer
9,078,792 B2 7/2015 Ruiz
9,145,879 B2 9/2015 Pirovano et al.
9,173,602 B2 11/2015 Gilbert
9,173,799 B2 * 11/2015 Tanimoto ................ A61F 5/453
9,187,220 B2 11/2015 Biesecker et al.
9,199,772 B2 12/2015 Krippendorf
9,233,020 B2 1/2016 Matsumiya
9,248,058 B2 2/2016 Conway et al.
9,308,118 B1 4/2016 Dupree et al.
9,309,029 B2 4/2016 Incorvia et al.
9,333,281 B2 5/2016 Giezendanner et al.
9,381,108 B2 7/2016 Longoni et al.
9,382,047 B2 7/2016 Schmidtner et al.
9,402,424 B2 8/2016 Roy
9,456,937 B2 * 10/2016 Ellis ...................... A61F 13/472
9,480,595 B2 11/2016 Baham et al.
9,517,865 B2 12/2016 Albers et al.
D777,941 S 1/2017 Piramoon
9,533,806 B2 1/2017 Ding et al.
9,550,611 B2 1/2017 Hodge
9,555,930 B2 1/2017 Campbell et al.
9,623,159 B2 4/2017 Locke
D789,522 S 6/2017 Burgess et al.
9,687,849 B2 6/2017 Bruno et al.
9,694,949 B2 7/2017 Hendricks et al.
9,709,048 B2 7/2017 Kinjo
9,713,547 B2 7/2017 Lee et al.
9,732,754 B2 8/2017 Huang et al.
9,752,564 B2 9/2017 Arceno et al.
9,788,992 B2 10/2017 Harvie
D804,907 S 12/2017 Sandoval
9,868,564 B2 1/2018 Mcgirr et al.
D814,239 S 4/2018 Arora
D817,484 S 5/2018 Lafond
10,037,640 B2 7/2018 Gordon
10,058,470 B2 8/2018 Phillips
10,098,990 B2 10/2018 Koch et al.
D835,264 S 12/2018 Mozzicato et al.
D835,779 S 12/2018 Mozzicato et al.
D840,533 S 2/2019 Mozzicato et al.
D840,534 S 2/2019 Mozzicato et al.
10,225,376 B2 3/2019 Perez Martinez
10,226,376 B2 * 3/2019 Sanchez .................. A61F 5/443
10,258,517 B1 4/2019 Maschino et al.
D848,612 S 5/2019 Mozzicato et al.
10,307,305 B1 6/2019 Hodges
10,335,121 B2 7/2019 Desai
D856,512 S 8/2019 Cowart et al.
10,376,406 B2 * 8/2019 Newton ................ A61F 5/4404
10,376,407 B2 8/2019 Newton
10,390,989 B2 * 8/2019 Sanchez ................. A61D 99/00
D858,144 S 9/2019 Fu
10,406,039 B2 9/2019 Villarreal
10,407,222 B2 9/2019 Allen
10,478,356 B2 11/2019 Griffin
10,500,108 B1 12/2019 Maschino et al.
10,538,366 B2 1/2020 Pentelovitch et al.
10,569,938 B2 2/2020 Zhao et al.
10,577,156 B2 3/2020 Dagnelie et al.
RE47,930 E 4/2020 Cho
10,618,721 B2 4/2020 Vazin
D884,390 S 5/2020 Wang
10,669,079 B2 6/2020 Freedman et al.
D892,315 S 8/2020 Airy
10,730,672 B2 8/2020 Bertram et al.
10,737,848 B2 8/2020 Philip et al.
10,765,854 B2 9/2020 Law et al.
10,766,670 B2 9/2020 Kittmann
10,799,386 B1 * 10/2020 Harrison, Sr. .......... A61F 5/441
10,806,642 B2 10/2020 Tagomori et al.
D901,214 S 11/2020 Hu
10,849,799 B2 12/2020 Nishikawa et al.
10,857,025 B2 * 12/2020 Davis ...................... A61F 5/451
10,865,017 B1 12/2020 Cowart et al.
10,889,412 B2 1/2021 West et al.
10,913,581 B2 2/2021 Stahlecker
D912,244 S 3/2021 Rehm et al.
10,952,889 B2 * 3/2021 Newton ................ A61F 5/4404
10,973,378 B2 4/2021 Ryu et al.
10,973,678 B2 * 4/2021 Newton .................. A61F 5/453
10,974,874 B2 4/2021 Ragias et al.
11,000,401 B2 5/2021 Ecklund et al.
D923,365 S 6/2021 Wang
11,026,829 B2 * 6/2021 Harvie .............. A61M 25/0017
11,027,900 B2 6/2021 Liu
11,045,346 B2 6/2021 Argent et al.
D928,946 S * 8/2021 Sanchez ....................... D24/122
11,090,183 B2 8/2021 Sanchez et al.
11,160,695 B2 11/2021 Febo et al.
11,160,697 B2 11/2021 Maschino et al.
11,168,420 B2 11/2021 Kinugasa et al.
11,179,506 B2 11/2021 Barr et al.
11,226,376 B2 1/2022 Yamauchi et al.
11,253,407 B2 2/2022 Miao et al.
11,326,586 B2 5/2022 Milner et al.
11,369,508 B2 6/2022 Ecklund et al.
11,369,524 B2 6/2022 Hubbard et al.
11,376,152 B2 * 7/2022 Sanchez ................. A61D 99/00
11,382,786 B2 * 7/2022 Sanchez ................ A61F 5/4404
11,382,788 B2 7/2022 Hjorth et al.
11,389,318 B2 7/2022 Radl et al.
11,395,871 B2 7/2022 Radl et al.
11,399,990 B2 8/2022 Suyama
11,426,303 B2 * 8/2022 Davis .................... A61F 5/4408
11,504,265 B2 11/2022 Godinez et al.
11,529,252 B2 * 12/2022 Glithero .................. A61F 5/455
11,547,788 B2 1/2023 Radl et al.
11,806,266 B2 11/2023 Sanchez et al.
11,839,567 B2 12/2023 Davis et al.
D1,010,109 S 1/2024 Ecklund et al.
11,857,716 B2 1/2024 Lee et al.
11,865,030 B2 1/2024 Davis et al.
11,890,221 B2 2/2024 Ulreich et al.
11,925,575 B2 * 3/2024 Newton .................. A61F 5/455
11,938,053 B2 3/2024 Austermann et al.
11,944,740 B2 4/2024 Hughett et al.
12,023,457 B2 7/2024 Mann et al.
12,042,422 B2 7/2024 Davis et al.
D1,038,385 S 8/2024 Ecklund et al.
12,245,966 B2 * 3/2025 Newton ................ A61F 5/4404
2001/0037097 A1 11/2001 Cheng et al.
2001/0054426 A1 12/2001 Knudson et al.
2002/0019614 A1 * 2/2002 Woon ................ A61F 13/53747 604/378
2002/0026161 A1 2/2002 Grundke
2002/0087131 A1 7/2002 Wolff et al.
2002/0091364 A1 7/2002 Prabhakar
2002/0189992 A1 12/2002 Schmidt et al.
2002/0193760 A1 12/2002 Thompson
2003/0004436 A1 1/2003 Schmidt et al.
2003/0032931 A1 2/2003 Grundke et al.
2003/0032944 A1 2/2003 Cawood
2003/0073964 A1 4/2003 Palumbo et al.
2003/0120178 A1 6/2003 Heki
2003/0157859 A1 8/2003 Ishikawa
2003/0181880 A1 9/2003 Schwartz
2003/0195484 A1 10/2003 Harvie

(56) References Cited

U.S. PATENT DOCUMENTS

2003/0204173 A1 10/2003 Burns et al.
2003/0233079 A1 12/2003 Parks et al.
2004/0006321 A1 1/2004 Cheng et al.
2004/0015141 A1 1/2004 Cheng et al.
2004/0056122 A1 3/2004 Male et al.
2004/0084465 A1 5/2004 Luburic
2004/0127872 A1 7/2004 Petryk et al.
2004/0128749 A1 7/2004 Scott
2004/0143229 A1* 7/2004 Easter .................... A61F 5/451 604/322
2004/0147863 A1 7/2004 Diaz et al.
2004/0147894 A1 7/2004 Mizutani et al.
2004/0158221 A1 8/2004 Mizutani et al.
2004/0176731 A1* 9/2004 Cheng .................... A61F 5/455 604/329
2004/0176746 A1 9/2004 Forral
2004/0191919 A1 9/2004 Unger et al.
2004/0200936 A1 10/2004 Opperthauser
2004/0207530 A1* 10/2004 Nielsen .................. A61F 13/42 340/573.5
2004/0236292 A1* 11/2004 Tazoe ..................... A61F 5/451 604/317
2004/0243075 A1 12/2004 Harvie
2004/0254547 A1* 12/2004 Okabe .................... A61F 5/455 604/317
2005/0010182 A1 1/2005 Parks et al.
2005/0033248 A1* 2/2005 Machida ................ A61F 5/455 604/327
2005/0065471 A1 3/2005 Kuntz
2005/0070861 A1* 3/2005 Okabe .................. A61F 5/4404 604/327
2005/0070862 A1* 3/2005 Tazoe ..................... A61F 5/455 604/327
2005/0082300 A1 4/2005 Modrell et al.
2005/0097662 A1 5/2005 Leimkuhler et al.
2005/0101924 A1 5/2005 Elson et al.
2005/0119630 A1 6/2005 Harvie
2005/0137557 A1 6/2005 Swiecicki et al.
2005/0154360 A1 7/2005 Harvie
2005/0177070 A1 8/2005 Levinson et al.
2005/0197639 A1 9/2005 Mombrinie
2005/0273920 A1 12/2005 Marinas
2005/0277904 A1 12/2005 Chase et al.
2005/0279359 A1 12/2005 Leblanc et al.
2006/0004332 A1 1/2006 Marx
2006/0015080 A1 1/2006 Mahnensmith
2006/0015081 A1* 1/2006 Suzuki .................... A61F 5/451 604/329
2006/0016778 A1 1/2006 Park
2006/0069359 A1 3/2006 Dipalma et al.
2006/0079854 A1 4/2006 Kay et al.
2006/0111648 A1* 5/2006 Vermaak ............. A61B 10/007 604/355
2006/0155214 A1* 7/2006 Wightman ............. A61F 5/455 600/574
2006/0171997 A1 8/2006 Gruenbacher et al.
2006/0200102 A1 9/2006 Cooper
2006/0229575 A1 10/2006 Boiarski
2006/0229576 A1 10/2006 Conway et al.
2006/0231648 A1 10/2006 Male et al.
2006/0235266 A1 10/2006 Nan
2006/0235359 A1 10/2006 Marland
2006/0241553 A1 10/2006 Harvie
2006/0269439 A1 11/2006 White
2006/0277670 A1 12/2006 Baker et al.
2007/0006368 A1 1/2007 Key et al.
2007/0010797 A1 1/2007 Nishtala et al.
2007/0016152 A1 1/2007 Karpowicz et al.
2007/0038194 A1* 2/2007 Wada ..................... A61F 5/451 604/347
2007/0055209 A1 3/2007 Patel et al.
2007/0073252 A1 3/2007 Forgrave
2007/0117880 A1 5/2007 Elson et al.
2007/0118993 A1 5/2007 Bates
2007/0135786 A1 6/2007 Schmidt et al.
2007/0137718 A1 6/2007 Rushlander et al.
2007/0149935 A1 6/2007 Dirico
2007/0191804 A1 8/2007 Coley
2007/0203464 A1 8/2007 Green et al.
2007/0214553 A1* 9/2007 Carromba ............. A47K 11/12 4/144.4
2007/0225663 A1 9/2007 Watt et al.
2007/0225666 A1 9/2007 Otto
2007/0225668 A1 9/2007 Otto
2007/0266486 A1 11/2007 Ramirez
2007/0282309 A1 12/2007 Bengtson et al.
2008/0004576 A1 1/2008 Tanaka et al.
2008/0015526 A1 1/2008 Reiner et al.
2008/0015527 A1 1/2008 House
2008/0033386 A1* 2/2008 Okabe .................. A61F 5/4404 604/378
2008/0041869 A1 2/2008 Backaert
2008/0091153 A1* 4/2008 Harvie .................... A61F 5/451 604/318
2008/0091158 A1 4/2008 Yang
2008/0114327 A1 5/2008 Barge
2008/0167634 A1 7/2008 Kouta et al.
2008/0183157 A1 7/2008 Walters
2008/0215031 A1 9/2008 Belfort et al.
2008/0234642 A1 9/2008 Patterson et al.
2008/0269703 A1 10/2008 Collins et al.
2008/0281282 A1 11/2008 Finger et al.
2008/0287894 A1* 11/2008 Van Den Heuvel .... A61F 5/455 604/327
2008/0312550 A1 12/2008 Nishtala et al.
2009/0025717 A1 1/2009 Pinel
2009/0048570 A1 2/2009 Jensen
2009/0056003 A1 3/2009 Ivie et al.
2009/0069761 A1 3/2009 Vogel
2009/0069765 A1 3/2009 Wortham
2009/0120179 A1 5/2009 Nylander et al.
2009/0192482 A1* 7/2009 Dodge, II ......... A61F 13/53708 524/436
2009/0234312 A1 9/2009 Otoole et al.
2009/0251510 A1 10/2009 Noro et al.
2009/0264840 A1 10/2009 Virginio
2009/0270822 A1* 10/2009 Medeiros ................ A61F 5/451 604/347
2009/0281510 A1 11/2009 Fisher
2009/0283982 A1 11/2009 Thomas
2010/0004612 A1* 1/2010 Thevenin ................ A61F 13/84 4/443
2010/0058660 A1 3/2010 Williams
2010/0121289 A1 5/2010 Parks et al.
2010/0158168 A1 6/2010 Murthy et al.
2010/0160882 A1 6/2010 Lowe
2010/0174250 A1 7/2010 Hu et al.
2010/0179493 A1 7/2010 Heagle et al.
2010/0185168 A1* 7/2010 Graauw ................ A61F 5/4556 604/347
2010/0198172 A1 8/2010 Wada et al.
2010/0211032 A1* 8/2010 Tsai ........................ A61F 5/453 604/319
2010/0234820 A1* 9/2010 Tsai ........................ A61M 1/87 604/385.03
2010/0241104 A1 9/2010 Gilbert
2010/0263113 A1 10/2010 Shelton et al.
2010/0310845 A1 12/2010 Bond et al.
2011/0028920 A1 2/2011 Johannison
2011/0028922 A1 2/2011 Kay et al.
2011/0034889 A1 2/2011 Smith
2011/0036837 A1 2/2011 Shang
2011/0040267 A1* 2/2011 Wada .................... A61F 5/4401 604/318
2011/0040271 A1* 2/2011 Rogers .................. A61F 5/4556 604/346
2011/0054426 A1 3/2011 Stewart et al.
2011/0060299 A1 3/2011 Wada et al.
2011/0060300 A1* 3/2011 Weig ....................... A61F 5/451 604/319
2011/0077495 A1 3/2011 Gilbert
2011/0077606 A1 3/2011 Wilcox et al.

(56) References Cited

U.S. PATENT DOCUMENTS

2011/0087337 A1 4/2011 Forsell
2011/0137273 A1 6/2011 Muellejans et al.
2011/0145993 A1 6/2011 Rader et al.
2011/0152802 A1 6/2011 Dicamillo et al.
2011/0164147 A1 7/2011 Takahashi et al.
2011/0172620 A1 7/2011 Khambatta
2011/0172625 A1* 7/2011 Wada .................... A61F 13/42 604/385.01
2011/0202024 A1 8/2011 Cozzens
2011/0238023 A1 9/2011 Slayton
2011/0240648 A1 10/2011 Tucker
2011/0251572 A1 10/2011 Nishtala et al.
2011/0265889 A1 11/2011 Tanaka et al.
2011/0276020 A1 11/2011 Mitsui
2012/0029452 A1 2/2012 Roedsten
2012/0035577 A1 2/2012 Tomes et al.
2012/0041400 A1 2/2012 Christensen
2012/0059328 A1 3/2012 Dikeman et al.
2012/0066825 A1 3/2012 Birbara et al.
2012/0103347 A1* 5/2012 Wheaton ................ A61F 5/453 128/885
2012/0137420 A1 6/2012 Gordon et al.
2012/0165768 A1 6/2012 Sekiyama et al.
2012/0165786 A1 6/2012 Chappa et al.
2012/0210503 A1* 8/2012 Anzivino, Sr. ....... A61F 5/4556 4/144.3
2012/0233761 A1 9/2012 Huang
2012/0245541 A1* 9/2012 Suzuki .................... A61F 13/42 604/319
2012/0245542 A1* 9/2012 Suzuki .................... A61F 13/84 374/45
2012/0245547 A1 9/2012 Wilcox et al.
2012/0253303 A1* 10/2012 Suzuki .................... A61F 13/42 374/45
2012/0271259 A1 10/2012 Ulert
2012/0296305 A1 11/2012 Barraza Khaled et al.
2012/0316522 A1 12/2012 Carter et al.
2012/0330256 A1 12/2012 Wilcox et al.
2013/0006206 A1* 1/2013 Wada .................... A61F 13/535 604/385.01
2013/0045651 A1 2/2013 Esteves et al.
2013/0053804 A1 2/2013 Soerensen et al.
2013/0096523 A1 4/2013 Chang et al.
2013/0110059 A1 5/2013 Kossow et al.
2013/0138064 A1 5/2013 Stroebech et al.
2013/0150813 A1 6/2013 Gordon et al.
2013/0218112 A1 8/2013 Thompson
2013/0245496 A1 9/2013 Wells et al.
2013/0245586 A1 9/2013 Jha
2013/0292537 A1 11/2013 Dirico
2013/0330501 A1 12/2013 Aizenberg et al.
2014/0005647 A1 1/2014 Shuffler et al.
2014/0031774 A1* 1/2014 Bengtson ................ A61M 1/90 604/319
2014/0039432 A1 2/2014 Dunbar et al.
2014/0107599 A1 4/2014 Fink et al.
2014/0157499 A1 6/2014 Suzuki et al.
2014/0171889 A1 6/2014 Hopman et al.
2014/0182051 A1* 7/2014 Tanimoto ............... A61G 9/006 4/144.3
2014/0196189 A1 7/2014 Lee et al.
2014/0276501 A1 9/2014 Cisko
2014/0303582 A1 10/2014 Wright et al.
2014/0316381 A1 10/2014 Reglin
2014/0325746 A1 11/2014 Block
2014/0348139 A1 11/2014 Gomez Martinez
2014/0352050 A1 12/2014 Yao et al.
2014/0371628 A1 12/2014 Desai
2015/0045757 A1 2/2015 Lee et al.
2015/0047114 A1 2/2015 Ramirez
2015/0048089 A1 2/2015 Robertson
2015/0135423 A1 5/2015 Sharpe et al.
2015/0157300 A1 6/2015 Ealovega et al.
2015/0209194 A1 7/2015 Heyman
2015/0290425 A1 10/2015 Macy et al.
2015/0320583 A1 11/2015 Harvie
2015/0329255 A1 11/2015 Rzepecki
2015/0342799 A1 12/2015 Michiels et al.
2015/0359660 A1* 12/2015 Harvie .................... A61F 5/441 604/351
2015/0366699 A1 12/2015 Nelson
2016/0029998 A1 2/2016 Brister et al.
2016/0030228 A1 2/2016 Jones
2016/0038356 A1 2/2016 Yao et al.
2016/0058322 A1 3/2016 Brister et al.
2016/0060001 A1 3/2016 Wada et al.
2016/0100976 A1 4/2016 Conway et al.
2016/0106604 A1* 4/2016 Timm .................... A61F 13/84 604/385.01
2016/0113809 A1 4/2016 Kim
2016/0183689 A1 6/2016 Miner
2016/0256022 A1 9/2016 Le
2016/0270982 A1 9/2016 Raycheck et al.
2016/0278662 A1 9/2016 Brister et al.
2016/0357400 A1 12/2016 Penha et al.
2016/0366699 A1 12/2016 Zhang et al.
2016/0367226 A1* 12/2016 Newton ............... A01K 23/005
2016/0367411 A1 12/2016 Justiz et al.
2016/0367726 A1 12/2016 Gratzer
2016/0374848 A1* 12/2016 Sanchez .................. A61F 5/455 604/319
2017/0007438 A1* 1/2017 Harvie .................... A61F 5/453
2017/0014560 A1 1/2017 Minskoff et al.
2017/0042748 A1 2/2017 Griffin
2017/0100276 A1 4/2017 Joh
2017/0128638 A1 5/2017 Giezendanner et al.
2017/0136209 A1 5/2017 Burnett et al.
2017/0143534 A1 5/2017 Sanchez
2017/0165100 A1 6/2017 Jackson et al.
2017/0165405 A1 6/2017 Muser et al.
2017/0189225 A1 7/2017 Voorhees et al.
2017/0202692 A1 7/2017 Laniado
2017/0216081 A1 8/2017 Accosta
2017/0246026 A1 8/2017 Laniado
2017/0252014 A1 9/2017 Siller Gonzalez et al.
2017/0252202 A9 9/2017 Sanchez et al.
2017/0266031 A1* 9/2017 Sanchez .................. A61F 5/443
2017/0266658 A1 9/2017 Bruno et al.
2017/0281399 A1* 10/2017 VanMiddendorp ..... A61M 1/80
2017/0312116 A1 11/2017 Laniado
2017/0325788 A1 11/2017 Ealovega et al.
2017/0333244 A1 11/2017 Laniado
2017/0348139 A1* 12/2017 Newton ................ A61F 5/4404
2017/0354532 A1 12/2017 Holt
2017/0354551 A1 12/2017 Gawley et al.
2017/0367873 A1 12/2017 Grannum
2018/0002075 A1 1/2018 Lee
2018/0008451 A1 1/2018 Stroebech
2018/0008804 A1 1/2018 Laniado
2018/0021218 A1 1/2018 Brosch et al.
2018/0028349 A1* 2/2018 Newton .................. A61M 1/88
2018/0037384 A1 2/2018 Archeny et al.
2018/0049910 A1 2/2018 Newton
2018/0064572 A1 3/2018 Wiltshire
2018/0104131 A1 4/2018 Killian
2018/0127187 A1 5/2018 Sewell
2018/0193215 A1 7/2018 Davies et al.
2018/0200101 A1 7/2018 Su
2018/0228642 A1* 8/2018 Davis ..................... A61B 5/208
2018/0256384 A1 9/2018 Kasirye
2018/0271694 A1 9/2018 Fernandez et al.
2018/0317892 A1 11/2018 Catlin
2018/0325748 A1 11/2018 Sharma et al.
2019/0001030 A1 1/2019 Braga et al.
2019/0021899 A1 1/2019 Vlet
2019/0038451 A1* 2/2019 Harvie .................... A61F 5/441
2019/0046102 A1 2/2019 Kushnir et al.
2019/0059938 A1 2/2019 Holsten
2019/0091059 A1 3/2019 Gabriel
2019/0100362 A1 4/2019 Meyers et al.
2019/0133814 A1 5/2019 Tammen et al.
2019/0142624 A1* 5/2019 Sanchez .................. A61F 5/453 604/319

(56) References Cited

U.S. PATENT DOCUMENTS

2019/0224036 A1* 7/2019 Sanchez .................. A61F 5/455
2019/0247222 A1 8/2019 Ecklund et al.
2019/0247223 A1 8/2019 Brun et al.
2019/0282391 A1 9/2019 Johannes et al.
2019/0314189 A1 10/2019 Acosta
2019/0314190 A1* 10/2019 Sanchez .................. A61F 5/443
2019/0321587 A1 10/2019 Mcmenamin et al.
2019/0344934 A1 11/2019 Faerber et al.
2019/0365307 A1 12/2019 Laing et al.
2019/0365561 A1 12/2019 Newton et al.
2019/0374373 A1 12/2019 Joh
2020/0008985 A1 1/2020 Nguyen et al.
2020/0016012 A1 1/2020 Dutkiewicz
2020/0030595 A1 1/2020 Boukidjian et al.
2020/0046544 A1* 2/2020 Godinez ................. A61F 5/455
2020/0055638 A1 2/2020 Lau et al.
2020/0070392 A1 3/2020 Huber et al.
2020/0085609 A1 3/2020 Schelch et al.
2020/0085610 A1 3/2020 Cohn et al.
2020/0086090 A1 3/2020 Von Weymarn-schärli et al.
2020/0107518 A1 4/2020 Hiroshima et al.
2020/0129322 A1 4/2020 Leuckel
2020/0171217 A9 6/2020 Braga et al.
2020/0206039 A1 7/2020 Mclain
2020/0214910 A1 7/2020 Varona et al.
2020/0216898 A1 7/2020 Hubbell
2020/0216989 A1 7/2020 Kinugasa et al.
2020/0229964 A1 7/2020 Staali et al.
2020/0231343 A1 7/2020 Freedman et al.
2020/0232841 A1 7/2020 Satish et al.
2020/0246172 A1 8/2020 Ho
2020/0246203 A1 8/2020 Tulk et al.
2020/0255189 A1 8/2020 Liu
2020/0261280 A1 8/2020 Heyman
2020/0276046 A1 9/2020 Staali et al.
2020/0306075 A1 10/2020 Newton et al.
2020/0315837 A1 10/2020 Radl et al.
2020/0315838 A1 10/2020 Eckert
2020/0315872 A1 10/2020 Viens et al.
2020/0315874 A1 10/2020 Viens et al.
2020/0331672 A1 10/2020 Bertram et al.
2020/0345332 A1 11/2020 Duval
2020/0353135 A1 11/2020 Gregory et al.
2020/0367677 A1 11/2020 Silsby et al.
2020/0369444 A1 11/2020 Silsby et al.
2020/0375781 A1* 12/2020 Staali ...................... A61M 1/71
2020/0375810 A1 12/2020 Carlin et al.
2020/0385179 A1 12/2020 Mccourt
2020/0390591 A1* 12/2020 Glithero ................ A61F 5/4401
2020/0390592 A1 12/2020 Merrill
2020/0405521 A1 12/2020 Glasroe
2021/0008771 A1 1/2021 Huber et al.
2021/0009323 A1 1/2021 Markarian et al.
2021/0020072 A1 1/2021 Moehring et al.
2021/0059853 A1* 3/2021 Davis ..................... A61B 5/208
2021/0061523 A1 3/2021 Bytheway
2021/0069005 A1* 3/2021 Sanchez .................. A61F 5/443
2021/0069008 A1* 3/2021 Blabas .................... A61F 5/455
2021/0069009 A1 3/2021 Im
2021/0069030 A1 3/2021 Nishikawa et al.
2021/0077993 A1 3/2021 Nazareth et al.
2021/0113749 A1 4/2021 Radl et al.
2021/0121318 A1 4/2021 Pinlac
2021/0137724 A1 5/2021 Ecklund et al.
2021/0138190 A1 5/2021 Erbey et al.
2021/0154055 A1 5/2021 Villarreal
2021/0170079 A1 6/2021 Radl et al.
2021/0178390 A1 6/2021 Oueslati et al.
2021/0186742 A1 6/2021 Newton et al.
2021/0212865 A1 7/2021 Wallajapet et al.
2021/0220162 A1* 7/2021 Jamison .................. A61F 5/453
2021/0220163 A1 7/2021 Mayrand
2021/0228400 A1 7/2021 Glithero
2021/0228401 A1 7/2021 Becker et al.
2021/0228795 A1* 7/2021 Hughett .................. A61F 5/451
2021/0229877 A1 7/2021 Ragias et al.
2021/0236323 A1* 8/2021 Austermann ........... A61F 5/453
2021/0236324 A1 8/2021 Sweeney
2021/0251814 A1 8/2021 Jönegren et al.
2021/0267787 A1 9/2021 Nazemi
2021/0275343 A1* 9/2021 Sanchez ................ A61F 5/4404
2021/0275344 A1 9/2021 Wing
2021/0290454 A1 9/2021 Yamada
2021/0315727 A1 10/2021 Jiang
2021/0353450 A1* 11/2021 Sharma ................. A61F 5/4408
2021/0361469 A1 11/2021 Liu et al.
2021/0369495 A1* 12/2021 Cheng ..................... A61F 5/451
2021/0386925 A1 12/2021 Hartwell et al.
2021/0393433 A1 12/2021 Godinez et al.
2022/0023091 A1 1/2022 Ecklund et al.
2022/0031523 A1 2/2022 Pierpoint
2022/0039995 A1 2/2022 Johannes et al.
2022/0047410 A1 2/2022 Walthall
2022/0062027 A1 3/2022 Mitchell et al.
2022/0062028 A1* 3/2022 Mitchell ............... A61F 5/4405
2022/0062029 A1* 3/2022 Johannes ............. A61F 5/4401
2022/0066825 A1 3/2022 Saraf et al.
2022/0071811 A1* 3/2022 Cheng ................... A61F 5/4404
2022/0071826 A1 3/2022 Kulkarni et al.
2022/0104965 A1 4/2022 Vaninetti et al.
2022/0104976 A1 4/2022 Hoeger et al.
2022/0104981 A1 4/2022 Jones
2022/0117773 A1 4/2022 Davis et al.
2022/0117774 A1* 4/2022 Meyer ..................... A61F 5/455
2022/0117775 A1* 4/2022 Jones .................... A61L 26/008
2022/0133524 A1* 5/2022 Davis ...................... A61M 1/60
604/319
2022/0151817 A1* 5/2022 Mann ...................... A61F 5/451
2022/0160949 A1 5/2022 Simiele et al.
2022/0168159 A1 6/2022 Triado et al.
2022/0193312 A1 6/2022 Lee et al.
2022/0211536 A1 7/2022 Johannes et al.
2022/0218510 A1 7/2022 Metzger et al.
2022/0229053 A1 7/2022 Levin et al.
2022/0241106 A1 8/2022 Johannes et al.
2022/0247407 A1 8/2022 Yamamoto et al.
2022/0248836 A1 8/2022 Cagle et al.
2022/0257407 A1* 8/2022 Johannes ................ A61F 5/453
2022/0265460 A1 8/2022 Coker
2022/0265462 A1* 8/2022 Alder ...................... A61F 5/455
2022/0270711 A1 8/2022 Feala et al.
2022/0273482 A1 9/2022 Johannes et al.
2022/0280357 A1* 9/2022 Jagannathan ........... A61F 13/84
2022/0287689 A1 9/2022 Johannes
2022/0287868 A1 9/2022 Garvey et al.
2022/0296408 A1 9/2022 Evans et al.
2022/0305191 A1 9/2022 Joseph et al.
2022/0313222 A1* 10/2022 Austermann ........ A61B 10/007
2022/0313474 A1 10/2022 Kriscovich et al.
2022/0331170 A1 10/2022 Erdem et al.
2022/0339024 A1 10/2022 Johannes et al.
2022/0354685 A1* 11/2022 Davis ..................... A61B 5/208
2022/0362049 A1 11/2022 Austermann et al.
2022/0370231 A1 11/2022 Wang et al.
2022/0370234 A1* 11/2022 Hughett .................. A61F 5/451
2022/0370235 A1* 11/2022 Johannes .............. A61F 5/4408
2022/0370237 A1 11/2022 Parmar et al.
2022/0387001 A1* 12/2022 Askenazi ................ A61F 5/455
2022/0395390 A1 12/2022 Brooks
2022/0395391 A1* 12/2022 Saunders .............. A61F 5/4404
2022/0409422 A1 12/2022 Schneider et al.
2023/0018845 A1 1/2023 Lee
2023/0020563 A1* 1/2023 Sharma ................... A61F 5/443
2023/0031640 A1 2/2023 Hughett et al.
2023/0037159 A1 2/2023 Brennan et al.
2023/0052238 A1 2/2023 Oluwasogo
2023/0062994 A1 3/2023 Ecklund et al.
2023/0070347 A1 3/2023 Watson et al.
2023/0073708 A1 3/2023 Xu et al.
2023/0089032 A1* 3/2023 Hughett .................. A61F 5/455
604/319
2023/0099821 A1 3/2023 Radl et al.
2023/0099991 A1 3/2023 Bianchi et al.
2023/0105001 A1 4/2023 Whittome et al.

(56) References Cited

U.S. PATENT DOCUMENTS

| | | | | |
|---|---|---|---|---|
| 2023/0110577 | A1 | 4/2023 | Choi | |
| 2023/0138269 | A1* | 5/2023 | Abdelal | A61F 5/451 604/347 |
| 2023/0145365 | A1 | 5/2023 | Martin et al. | |
| 2023/0155253 | A1 | 5/2023 | Yin et al. | |
| 2023/0210504 | A1 | 7/2023 | Kuroda et al. | |
| 2023/0210685 | A1 | 7/2023 | Fallows et al. | |
| 2023/0218426 | A1 | 7/2023 | Hughett | |
| 2023/0240884 | A1 | 8/2023 | Davis et al. | |
| 2023/0248562 | A1 | 8/2023 | Sanchez et al. | |
| 2023/0248564 | A1 | 8/2023 | Mann et al. | |
| 2023/0255812 | A1 | 8/2023 | Sanchez et al. | |
| 2023/0255813 | A1 | 8/2023 | Sanchez et al. | |
| 2023/0255815 | A1 | 8/2023 | Newton | |
| 2023/0263650 | A1 | 8/2023 | Sanchez et al. | |
| 2023/0263655 | A1 | 8/2023 | Johannes et al. | |
| 2023/0277362 | A1* | 9/2023 | Davis | A61B 5/208 604/319 |
| 2023/0285178 | A1 | 9/2023 | Sanchez et al. | |
| 2023/0293339 | A1 | 9/2023 | James | |
| 2023/0301846 | A1 | 9/2023 | Greenwood | |
| 2023/0355423 | A1 | 11/2023 | Stevenson et al. | |
| 2023/0404791 | A1 | 12/2023 | Ecklund et al. | |
| 2024/0008444 | A1 | 1/2024 | Su et al. | |
| 2024/0009023 | A1 | 1/2024 | Johannes et al. | |
| 2024/0024170 | A1 | 1/2024 | Scott | |
| 2024/0041638 | A1 | 2/2024 | Johannes et al. | |
| 2024/0058161 | A1 | 2/2024 | Ulreich et al. | |
| 2024/0065881 | A1 | 2/2024 | Kuroda et al. | |
| 2024/0099874 | A1 | 3/2024 | Sanchez et al. | |
| 2024/0110318 | A1 | 4/2024 | Bendt et al. | |
| 2024/0123134 | A1 | 4/2024 | Kharkar et al. | |
| 2024/0148539 | A1* | 5/2024 | Austermann | A61F 5/455 |
| 2024/0261131 | A1 | 8/2024 | Garvey et al. | |

FOREIGN PATENT DOCUMENTS

| | | | |
|---|---|---|---|
| CA | 2165286 | C | 9/1999 |
| CA | 2354132 | A1 | 6/2000 |
| CA | 2359091 | C | 9/2003 |
| CA | 2488867 | C | 8/2007 |
| CA | 3050918 | A1 | 8/2018 |
| CA | 3098571 | A1 | 11/2019 |
| CN | 2269203 | Y | 12/1997 |
| CN | 1332620 | A | 1/2002 |
| CN | 1434693 | A | 8/2003 |
| CN | 1533755 | A | 10/2004 |
| CN | 1602825 | A | 4/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 103533968 | A | 1/2014 |
| CN | 103717180 | A | 4/2014 |
| CN | 204562697 | U | 8/2015 |
| CN | 105411783 | A | 3/2016 |
| CN | 105451693 | A | 3/2016 |
| CN | 105534632 | A | 5/2016 |
| CN | 205849719 | U | 1/2017 |
| CN | 106726089 | A | 5/2017 |
| CN | 107847384 | A | 3/2018 |
| CN | 107920912 | A | 4/2018 |
| CN | 108420590 | A | 8/2018 |
| CN | 209285902 | U | 8/2019 |
| CN | 110381883 | A | 10/2019 |
| CN | 211198839 | U | 8/2020 |
| CN | 112566550 | A | 3/2021 |
| CN | 112603184 | A | 4/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 4416094 | A1 | 11/1995 |
| DE | 4236097 | C2 | 10/1996 |
| DE | 19619597 | A1 | 11/1997 |
| DE | 102005037762 | B3 | 9/2006 |
| DE | 102011103783 | A1 | 12/2012 |
| DE | 202015104597 | U1 | 7/2016 |
| DE | 102020121462 | B3 | 1/2022 |
| DK | 9600118 | | 11/1996 |
| EP | 0032138 | A2 | 7/1981 |
| EP | 0066070 | B1 | 12/1982 |
| EP | 0068712 | A1 | 1/1983 |
| EP | 0140470 | A1 | 5/1985 |
| EP | 0140471 | B1 | 5/1988 |
| EP | 0274753 | A2 | 7/1988 |
| EP | 0119143 | B1 | 11/1988 |
| EP | 0483592 | A1 | 5/1992 |
| EP | 0610638 | A1 | 8/1994 |
| EP | 0613355 | A1 | 9/1994 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 3787570 | B1 | 3/2022 |
| EP | 4025163 | A1 | 7/2022 |
| EP | 3463180 | B1 | 3/2023 |
| EP | 3569205 | B1 | 6/2023 |
| EP | 4382082 | A2 | 6/2024 |
| GB | 871820 | A | 7/1961 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2181953 | A | 5/1987 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| GB | 2612752 | A | 5/2023 |
| IT | 201800009129 | A1 | 4/2020 |
| JP | S498638 | U | 1/1974 |
| JP | S5410596 | A | 1/1979 |
| JP | S5410596 | Y2 | 5/1979 |
| JP | S55155618 | A | 12/1980 |
| JP | S56152629 | U | 11/1981 |

(56) References Cited

FOREIGN PATENT DOCUMENTS

| | | | |
|---|---|---|---|
| JP | S5888596 | U | 6/1983 |
| JP | S63107780 | U | 7/1988 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H05123349 | A | 5/1993 |
| JP | H05123350 | A | 5/1993 |
| JP | 3087938 | B2 | 10/1995 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |
| JP | 2000116690 | A | 4/2000 |
| JP | 2000185068 | A | 7/2000 |
| JP | 2001054531 | A | 2/2001 |
| JP | 2001070331 | A | 3/2001 |
| JP | 2001224616 | A | 8/2001 |
| JP | 2001276107 | A | 10/2001 |
| JP | 2001276108 | A | 10/2001 |
| JP | 2002028173 | A | 1/2002 |
| JP | 2003505152 | A | 2/2003 |
| JP | 2003126242 | A | 5/2003 |
| JP | 2003180722 | A | 7/2003 |
| JP | 2003528691 | A | 9/2003 |
| JP | 2004057578 | A | 2/2004 |
| JP | 2004130056 | A | 4/2004 |
| JP | 2004267530 | A | 9/2004 |
| JP | 2005052219 | A | 3/2005 |
| JP | 2005066011 | A | 3/2005 |
| JP | 2005066325 | A | 3/2005 |
| JP | 2005102978 | A | 4/2005 |
| JP | 2005518237 | A | 6/2005 |
| JP | 3749097 | B2 | 12/2005 |
| JP | 2006026108 | A | 2/2006 |
| JP | 3123547 | B2 | 6/2006 |
| JP | 2006136492 | A | 6/2006 |
| JP | 2006204868 | A | 8/2006 |
| JP | 2007044494 | A | 2/2007 |
| JP | 3132659 | B2 | 5/2007 |
| JP | 2007209687 | A | 8/2007 |
| JP | 4039641 | B2 | 11/2007 |
| JP | 2008005975 | A | 1/2008 |
| JP | 2009509570 | A | 3/2009 |
| JP | 2009165887 | A | 7/2009 |
| JP | 2009525776 | A | 7/2009 |
| JP | 2010504150 | A | 2/2010 |
| JP | 2010081981 | A | 4/2010 |
| JP | 4640772 | B2 | 12/2010 |
| JP | 2010536439 | A | 12/2010 |
| JP | 2011500225 | A | 1/2011 |
| JP | 2011030962 | A | 2/2011 |
| JP | 4747166 | B2 | 5/2011 |
| JP | 2011087823 | A | 5/2011 |
| JP | 4801218 | B1 | 8/2011 |
| JP | 2011218130 | A | 11/2011 |
| JP | 2011224070 | A | 11/2011 |
| JP | 3175719 | U | 4/2012 |
| JP | 2012523869 | A | 10/2012 |
| JP | 2013238608 | A | 11/2013 |
| JP | 2014521960 | A | 8/2014 |
| JP | 2015092945 | A | 5/2015 |
| JP | 3198994 | B2 | 7/2015 |
| JP | 2016521191 | A | 7/2016 |
| JP | 2017014698 | A | 1/2017 |
| JP | 2019525811 | A | 9/2019 |
| JP | 2019170942 | A | 10/2019 |
| JP | 2019533492 | A | 11/2019 |
| JP | 2021120686 | A | 8/2021 |
| JP | 2021522009 | A | 8/2021 |
| JP | 2021522013 | A | 8/2021 |
| JP | 7129493 | B2 | 8/2022 |
| JP | 2023532132 | A | 7/2023 |
| KR | 200290061 | Y1 | 9/2002 |
| KR | 20030047451 | A | 6/2003 |
| KR | 20140039485 | A | 4/2014 |
| KR | 101432639 | B1 | 8/2014 |
| KR | 20180106659 | A | 10/2018 |
| KR | 20180108774 | A | 10/2018 |
| PT | 2068717 | E | 6/2013 |
| SE | 505542 | C2 | 9/1997 |
| WO | 8101957 | A1 | 7/1981 |
| WO | 8804558 | A1 | 6/1988 |
| WO | 9104714 | A2 | 4/1991 |
| WO | 9104714 | A3 | 6/1991 |
| WO | 9220299 | A3 | 2/1993 |
| WO | 9307839 | A1 | 4/1993 |
| WO | 9309736 | A2 | 5/1993 |
| WO | 9309736 | A3 | 6/1993 |
| WO | 9514448 | A2 | 6/1995 |
| WO | 9600096 | A1 | 1/1996 |
| WO | 9634636 | A1 | 11/1996 |
| WO | 9817211 | A1 | 4/1998 |
| WO | 9830336 | A1 | 7/1998 |
| WO | 0000112 | A1 | 1/2000 |
| WO | 0000113 | A1 | 1/2000 |
| WO | 0025651 | A1 | 5/2000 |
| WO | 0033773 | A1 | 6/2000 |
| WO | 0057784 | A1 | 10/2000 |
| WO | 0069377 | A1 | 11/2000 |
| WO | 0079497 | A1 | 12/2000 |
| WO | 0145618 | A1 | 6/2001 |
| WO | 0145621 | A1 | 6/2001 |
| WO | 02094160 | A1 | 11/2002 |
| WO | 03013967 | A1 | 2/2003 |
| WO | 03024824 | A1 | 3/2003 |
| WO | 03055423 | A1 | 7/2003 |
| WO | 03071931 | A2 | 9/2003 |
| WO | 03079942 | A1 | 10/2003 |
| WO | 03071931 | A3 | 2/2004 |
| WO | 2004019836 | A1 | 3/2004 |
| WO | 2004024046 | A1 | 3/2004 |
| WO | 2004026195 | A1 | 4/2004 |
| WO | 2005051252 | A1 | 6/2005 |
| WO | 2005074571 | A3 | 9/2005 |
| WO | 2005089687 | A2 | 9/2005 |
| WO | 2005107661 | A2 | 11/2005 |
| WO | 2006021220 | A1 | 3/2006 |
| WO | 2006037140 | A2 | 4/2006 |
| WO | 2007005851 | A2 | 1/2007 |
| WO | 2007007845 | A1 | 1/2007 |
| WO | 2007042823 | A2 | 4/2007 |
| WO | 2007055651 | A1 | 5/2007 |
| WO | 2006098950 | A3 | 11/2007 |
| WO | 2007134608 | A2 | 11/2007 |
| WO | 2007128156 | A3 | 2/2008 |
| WO | 2008026106 | A2 | 3/2008 |
| WO | 2008078117 | A1 | 7/2008 |
| WO | 2008104019 | A1 | 9/2008 |
| WO | 2008141471 | A1 | 11/2008 |
| WO | 2009004368 | A1 | 1/2009 |
| WO | 2009004369 | A1 | 1/2009 |
| WO | 2009052496 | A1 | 4/2009 |
| WO | 2009052502 | A1 | 4/2009 |
| WO | 2009007702 | A4 | 7/2009 |
| WO | 2009101738 | A1 | 8/2009 |
| WO | 2010058192 | A1 | 5/2010 |
| WO | 2010030122 | A3 | 7/2010 |
| WO | 2010101915 | A3 | 1/2011 |
| WO | 2011018132 | A1 | 2/2011 |
| WO | 2011018133 | A1 | 2/2011 |
| WO | 2011024864 | A1 | 3/2011 |
| WO | 2011054118 | A1 | 5/2011 |
| WO | 2011079132 | A1 | 6/2011 |
| WO | 2011107972 | A1 | 9/2011 |
| WO | 2011108972 | A1 | 9/2011 |
| WO | 2011117292 | A1 | 9/2011 |
| WO | 2011123219 | A1 | 10/2011 |
| WO | 2011132043 | A1 | 10/2011 |
| WO | 2012012908 | A1 | 2/2012 |
| WO | 2012065274 | A1 | 5/2012 |
| WO | 2012097462 | A1 | 7/2012 |

(56) References Cited

FOREIGN PATENT DOCUMENTS

| | | | |
|---|---|---|---|
| WO | 2012098796 A1 | 7/2012 | |
| WO | 2012101288 A1 | 8/2012 | |
| WO | 2012175916 A1 | 12/2012 | |
| WO | 2013018435 A1 | 2/2013 | |
| WO | 2013033429 A1 | 3/2013 | |
| WO | 2013055434 A1 | 4/2013 | |
| WO | 2013082397 A1 | 6/2013 | |
| WO | 2013103291 A2 | 7/2013 | |
| WO | 2013131109 A1 | 9/2013 | |
| WO | 2013167478 A1 | 11/2013 | |
| WO | 2013177716 A1 | 12/2013 | |
| WO | 2014041534 A1 | 3/2014 | |
| WO | 2014046420 A1 | 3/2014 | |
| WO | 2014118518 A1 | 8/2014 | |
| WO | 2014160852 A1 | 10/2014 | |
| WO | 2015023599 A1 | 2/2015 | |
| WO | 2015052348 A1 | 4/2015 | |
| WO | 2015068384 A1 | 5/2015 | |
| WO | 2015169403 A1 | 11/2015 | |
| WO | 2015170307 A1 | 11/2015 | |
| WO | 2015197462 A1 | 12/2015 | |
| WO | 2016051385 A1 | 4/2016 | |
| WO | 2016055989 A1 | 4/2016 | |
| WO | 2016071894 A1 | 5/2016 | |
| WO | 2016103242 A1 | 6/2016 | |
| WO | 2016116915 A1 | 7/2016 | |
| WO | 2016124203 A1 | 8/2016 | |
| WO | 2016139448 A1 | 9/2016 | |
| WO | 2016166562 A1 | 10/2016 | |
| WO | 2016167535 A1 | 10/2016 | |
| WO | 2016191574 A1 | 12/2016 | |
| WO | 2016200088 A1 | 12/2016 | |
| WO | 2016200361 A1 | 12/2016 | |
| WO | 2016204731 A1 | 12/2016 | |
| WO | 2017001532 A2 | 1/2017 | |
| WO | 2017001846 A1 | 1/2017 | |
| WO | 2017075226 A1 | 5/2017 | |
| WO | 2017152198 A1 | 9/2017 | |
| WO | 2017153357 A1 | 9/2017 | |
| WO | 2017162559 A1 | 9/2017 | |
| WO | 2017205446 A1 | 11/2017 | |
| WO | 2017209779 A1 | 12/2017 | |
| WO | 2017210524 A1 | 12/2017 | |
| WO | 2018022414 A1 | 2/2018 | |
| WO | 2018044781 A1 | 3/2018 | |
| WO | 2018056953 A1 | 3/2018 | |
| WO | 2018090550 A1 | 5/2018 | |
| WO | 2018138513 A1 | 8/2018 | |
| WO | 2018144318 A1 | 8/2018 | |
| WO | 2018144463 A1 | 8/2018 | |
| WO | 2018150263 A1 | 8/2018 | |
| WO | 2018150268 A1 | 8/2018 | |
| WO | 2018152156 A1 | 8/2018 | |
| WO | 2018183791 A1 | 10/2018 | |
| WO | 2018150267 A3 | 11/2018 | |
| WO | 2018235026 A1 | 12/2018 | |
| WO | 2018235065 A1 | 12/2018 | |
| WO | 2019004404 A1 | 1/2019 | |
| WO | 2019041005 A1 | 3/2019 | |
| WO | 2019044217 A1 | 3/2019 | |
| WO | 2019044218 A1 | 3/2019 | |
| WO | 2019044219 A1 | 3/2019 | |
| WO | 2019050959 A1 | 3/2019 | |
| WO | 2019065541 A1 | 4/2019 | |
| WO | 2019096845 A1 | 5/2019 | |
| WO | 2019150385 A1 | 8/2019 | |
| WO | 2019161094 A1 | 8/2019 | |
| WO | 2019188566 A1 | 10/2019 | |
| WO | 2019190593 A1 | 10/2019 | |
| WO | 2019212949 A1 | 11/2019 | |
| WO | 2019212950 A1 | 11/2019 | |
| WO | 2019212951 A1 | 11/2019 | |
| WO | 2019212952 A1 | 11/2019 | |
| WO | 2019212955 A1 | 11/2019 | |
| WO | 2019212956 A1 | 11/2019 | |
| WO | 2019214787 A1 | 11/2019 | |
| WO | 2019214788 A1 | 11/2019 | |
| WO | 2019226826 A1 | 11/2019 | |
| WO | WO-2019212954 A1 * | 11/2019 | ............ A61F 5/451 |
| WO | 2019239433 A1 | 12/2019 | |
| WO | 2020000994 A1 | 1/2020 | |
| WO | 2020020618 A1 | 1/2020 | |
| WO | 2020038822 A1 | 2/2020 | |
| WO | 2020088409 A1 | 5/2020 | |
| WO | 2020049394 A3 | 6/2020 | |
| WO | 2020120657 A1 | 6/2020 | |
| WO | 2020152575 A1 | 7/2020 | |
| WO | 2020182923 A1 | 9/2020 | |
| WO | 2020204967 A1 | 10/2020 | |
| WO | 2020205939 A1 | 10/2020 | |
| WO | 2020209898 A1 | 10/2020 | |
| WO | 2020242790 A1 | 12/2020 | |
| WO | 2020251893 A1 | 12/2020 | |
| WO | 2020256865 A1 | 12/2020 | |
| WO | 2021007144 A1 | 1/2021 | |
| WO | 2021007345 A1 | 1/2021 | |
| WO | 2021010844 A1 | 1/2021 | |
| WO | 2021016026 A1 | 1/2021 | |
| WO | 2021016300 A1 | 1/2021 | |
| WO | 2021025919 A1 | 2/2021 | |
| WO | 2021034886 A1 | 2/2021 | |
| WO | 2021041123 A1 | 3/2021 | |
| WO | 2021046501 A1 | 3/2021 | |
| WO | 2021086868 A1 | 5/2021 | |
| WO | 2021094352 A1 | 5/2021 | |
| WO | 2021094639 A1 | 5/2021 | |
| WO | 2021097067 A1 | 5/2021 | |
| WO | 2021102296 A1 | 5/2021 | |
| WO | 2021107025 A1 | 6/2021 | |
| WO | 2021138411 A1 | 7/2021 | |
| WO | 2021138414 A1 | 7/2021 | |
| WO | 2021154686 A1 | 8/2021 | |
| WO | 2021155206 A1 | 8/2021 | |
| WO | 2021170075 A1 | 9/2021 | |
| WO | 2021173436 A1 | 9/2021 | |
| WO | 2021188817 A1 | 9/2021 | |
| WO | 2021195384 A1 | 9/2021 | |
| WO | 2021205995 A1 | 10/2021 | |
| WO | 2021207621 A1 | 10/2021 | |
| WO | 2021211568 A1 | 10/2021 | |
| WO | 2021211801 A1 | 10/2021 | |
| WO | 2021211914 A1 | 10/2021 | |
| WO | 2021216419 A1 | 10/2021 | |
| WO | 2021216422 A1 | 10/2021 | |
| WO | 2021231532 A1 | 11/2021 | |
| WO | 2021247523 A1 | 12/2021 | |
| WO | 2021257202 A1 | 12/2021 | |
| WO | 2022006256 A1 | 1/2022 | |
| WO | 2022031943 A1 | 2/2022 | |
| WO | 2022035745 A1 | 2/2022 | |
| WO | 2022051360 A1 | 3/2022 | |
| WO | 2022054613 A1 | 3/2022 | |
| WO | 2022066704 A1 | 3/2022 | |
| WO | 2022067392 A1 | 4/2022 | |
| WO | 2022069950 A1 | 4/2022 | |
| WO | 2022071429 A1 | 4/2022 | |
| WO | 2022076322 A1 | 4/2022 | |
| WO | 2022076427 A2 | 4/2022 | |
| WO | 2022086898 A1 | 4/2022 | |
| WO | 2022090199 A1 | 5/2022 | |
| WO | 2022098536 A1 | 5/2022 | |
| WO | 2022099087 A1 | 5/2022 | |
| WO | 2022101999 A1 | 5/2022 | |
| WO | 2022115692 A1 | 6/2022 | |
| WO | 2022125685 A1 | 6/2022 | |
| WO | 2022140545 A1 | 6/2022 | |
| WO | 2022145231 A1 | 7/2022 | |
| WO | 2022150360 A1 | 7/2022 | |
| WO | 2022150463 A1 | 7/2022 | |
| WO | 2022159392 A1 | 7/2022 | |
| WO | 2022170182 A1 | 8/2022 | |
| WO | 2022182385 A1 | 9/2022 | |
| WO | 2022187152 A1 | 9/2022 | |
| WO | 2022192188 A1 | 9/2022 | |

(56) References Cited

FOREIGN PATENT DOCUMENTS

| | | | |
|---|---|---|---|
| WO | 2022192347 | A1 | 9/2022 |
| WO | 2022204000 | A1 | 9/2022 |
| WO | 2022216507 | A1 | 10/2022 |
| WO | 2022222030 | A1 | 10/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023023777 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |
| WO | 2023149903 | A1 | 8/2023 |
| WO | 2023154390 | A1 | 8/2023 |
| WO | 2023191764 | A1 | 10/2023 |
| WO | 2023244238 | A1 | 12/2023 |
| WO | 2024058788 | A1 | 3/2024 |

OTHER PUBLICATIONS

Corrected Notice of Allowability for U.S. Appl. No. 17/501,591 mailed Aug. 9, 2024.
Corrected Notice of Allowability for U.S. Appl. No. 17/664,914 mailed Aug. 9, 2024.
Final Office Action for U.S. Appl. No. 16/433,773 mailed Sep. 9, 2024.
Final Office Action for U.S. Appl. No. 17/446,256 mailed Aug. 7, 2024.
Final Office Action for U.S. Appl. No. 17/653,137 mailed Aug. 7, 2024.
Final Office Action for U.S. Appl. No. 17/653,920 mailed Aug. 14, 2024.
Final Office Action for U.S. Appl. No. 18/134,857 mailed Jul. 25, 2024.
International Search Report and Written Opinion from International Application No. PCT/US2023/036238 mailed Jul. 22, 2024.
International Search Report and Written Opinion from International Application No. PCT/US2023/077168 mailed Jun. 24, 2024.
International Search Report and Written Opinion from International Application No. PCT/US2023/080680 mailed Jul. 22, 2024.
Issue Notification for U.S. Appl. No. 17/453,560 mailed Aug. 7, 2024.
Non-Final Office Action for U.S. Appl. No. 16/478,180 mailed Aug. 7, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/645,821 mailed Sep. 6, 2024.
Non-Final Office Action for U.S. Appl. No. 17/653,314 mailed Aug. 29, 2024.
Non-Final Office Action for U.S. Appl. No. 17/749,340 mailed Aug. 14, 2024.
Non-Final Office Action for U.S. Appl. No. 17/758,316 mailed Aug. 28, 2024.
Non-Final Office Action for U.S. Appl. No. 18/139,523 mailed Aug. 26, 2024.
Non-Final Office Action for U.S. Appl. No. 18/426,795 mailed Aug. 9, 2024.
Non-Final Office Action for U.S. Appl. No. 18/451,080 mailed Jul. 30, 2024.
Notice of Allowance for U.S. Appl. No. 17/179,116 mailed Sep. 13, 2024.
Notice of Allowance for U.S. Appl. No. 17/447,123 mailed Jul. 26, 2024.
Notice of Allowance for U.S. Appl. No. 17/501,591 mailed Jul. 31, 2024.
Notice of Allowance for U.S. Appl. No. 17/664,914 mailed Jul. 26, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/198,464 mailed Jul. 30, 2024.
Notice of Allowance for U.S. Appl. No. 18/389,009 mailed Aug. 28, 2024.
Restriction Requirement for U.S. Appl. No. 17/625,941 mailed Aug. 7, 2024.
U.S. Appl. No. 15/611,587, filed Jun. 1, 2017.
U.S. Appl. No. 17/013,822, filed Sep. 7, 2020.
U.S. Appl. No. 18/828,559, filed Sep. 9, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
U.S. Appl. No. 18/841,630, filed Aug. 26, 2024.
U.S. Appl. No. 18/886,306, filed Sep. 16, 2024.
U.S. Appl. No. 63/568,615, filed Mar. 22, 2024.
U.S. Appl. No. 63/683,428, filed Aug. 15, 2024.
Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Dec. 29, 2023.
Advisory Action for U.S. Appl. No. 16/433,773 mailed Feb. 15, 2023.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 16/478,180 mailed Sep. 7, 2023.
Advisory Action for U.S. Appl. No. 16/904,868 mailed Jan. 2, 2024.
Advisory Action for U.S. Appl. No. 17/051,550 mailed Sep. 8, 2023.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/444,792 mailed Aug. 25, 2023.
Advisory Action for U.S. Appl. No. 17/444,792 mailed Jul. 8, 2024.
Advisory Action for U.S. Appl. No. 17/446,256 mailed Dec. 8, 2023.
Advisory Action for U.S. Appl. No. 17/446,654 mailed Apr. 15, 2024.
Advisory Action for U.S. Appl. No. 17/448,811 mailed Nov. 15, 2023.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/451,345 mailed Oct. 20, 2023.
Advisory Action for U.S. Appl. No. 17/451,354 mailed Jan. 30, 2024.
Advisory Action for U.S. Appl. No. 17/453,260 mailed Dec. 22, 2023.
Advisory Action for U.S. Appl. No. 17/501,591 mailed Feb. 22, 2024.
Advisory Action for U.S. Appl. No. 17/645,821 mailed Jul. 2, 2024.
Advisory Action for U.S. Appl. No. 17/646,771 mailed Feb. 29, 2024.
Advisory Action for U.S. Appl. No. 17/653,137 mailed Dec. 1, 2023.

(56) References Cited

OTHER PUBLICATIONS

Advisory Action for U.S. Appl. No. 17/655,464 mailed Dec. 13, 2023.
Advisory Action for U.S. Appl. No. 17/661,090 mailed Feb. 26, 2024.
Advisory Action for U.S. Appl. No. 17/662,700 mailed Jan. 30, 2023.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Communication of Notice of Opposition of European Application No. 17807547.9 mailed Jan. 5, 2024.
Corrected Notice of Allowability for U.S. Appl. No. 16/369,676 mailed Dec. 7, 2023.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/478,180 mailed Feb. 28, 2024.
Final Office Action for U.S. Appl. No. 16/478,180 mailed May 31, 2023.
Final Office Action for U.S. Appl. No. 16/904,868 mailed Nov. 2, 2023.
Final Office Action for U.S. Appl. No. 17/051,399 mailed Jan. 8, 2024.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/051,585 mailed Jul. 5, 2024.
Final Office Action for U.S. Appl. No. 17/051,600 mailed Jun. 27, 2024.
Final Office Action for U.S. Appl. No. 17/179,116 mailed Oct. 31, 2023.
Final Office Action for U.S. Appl. No. 17/444,792 mailed Apr. 3, 2024.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/448,811 mailed Aug. 3, 2023.
Final Office Action for U.S. Appl. No. 17/450,864 mailed Dec. 28, 2023.
Final Office Action for U.S. Appl. No. 17/451,345 mailed Apr. 18, 2024.
Final Office Action for U.S. Appl. No. 17/451,345 mailed May 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/645,821 mailed Apr. 3, 2024.
Final Office Action for U.S. Appl. No. 17/646,771 mailed Dec. 21, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 17/663,330 mailed Dec. 12, 2023.
Final Office Action for U.S. Appl. No. 17/664,487 mailed Jan. 4, 2024.
Final Office Action for U.S. Appl. No. 17/808,354 mailed Apr. 10, 2024.
Final Office Action for U.S. Appl. No. 18/139,523 mailed Dec. 22, 2023.
Final Office Action for U.S. Appl. No. 18/140,163 mailed Mar. 27, 2024.
Final Office Action for U.S. Appl. No. 18/140,751 mailed Jan. 17, 2024.
Final Office Action for U.S. Appl. No. 18/164,800 mailed Dec. 6, 2023.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
International Search Report and Written Opinion from International Application No. PCT/US2023/024805 mailed Dec. 14, 2023.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.

(56) References Cited

OTHER PUBLICATIONS

International Search Report and Written Opinion from International Application No. PCT/US2023/030373 mailed Mar. 13, 2024.
International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/036868 mailed Jun. 5, 2024.
International Search Report and Written Opinion from International Application No. PCT/US2023/075507 mailed Jun. 13, 2024.
International Search Report and Written Opinion from International Application No. PCT/US2023/077208 mailed May 10, 2024.
Issue Notification for U.S. Appl. No. 16/245,726 mailed Oct. 18, 2023.
Issue Notification for U.S. Appl. No. 16/449,039 mailed Jun. 19, 2024.
Issue Notification for U.S. Appl. No. 16/899,956 mailed Mar. 29, 2023.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/326,980 mailed Jul. 10, 2024.
Issue Notification for U.S. Appl. No. 17/448,811 mailed Jul. 3, 2024.
Issue Notification for U.S. Appl. No. 17/453,260 mailed Jul. 10, 2024.
Issue Notification for U.S. Appl. No. 17/461,036 mailed Oct. 11, 2023.
Issue Notification for U.S. Appl. No. 17/657,474 mailed Jun. 19, 2024.
Issue Notification for U.S. Appl. No. 17/663,046 mailed Dec. 20, 2023.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Apr. 11, 2023.
Non-Final Office Action for U.S. Appl. No. 16/433,773 mailed Feb. 26, 2024.
Non-Final Office Action for U.S. Appl. No. 16/449,039 mailed Apr. 27, 2023.
Non-Final Office Action for U.S. Appl. No. 16/452,145 mailed Mar. 28, 2023.
Non-Final Office Action for U.S. Appl. No. 16/452,145 mailed Nov. 2, 2023.
Non-Final Office Action for U.S. Appl. No. 16/452,258 mailed Apr. 26, 2023.
Non-Final Office Action for U.S. Appl. No. 16/452,258 mailed Jun. 20, 2024.
Non-Final Office Action for U.S. Appl. No. 16/478,180 mailed Nov. 7, 2023.
Non-Final Office Action for U.S. Appl. No. 16/904,868 mailed Mar. 12, 2024.
Non-Final Office Action for U.S. Appl. No. 16/904,868 mailed Mar. 15, 2023.
Non-Final Office Action for U.S. Appl. No. 17/051,399 mailed Aug. 18, 2023.
Non-Final Office Action for U.S. Appl. No. 17/051,550 mailed Oct. 24, 2023.
Non-Final Office Action for U.S. Appl. No. 17/051,585 mailed Jan. 8, 2024.
Non-Final Office Action for U.S. Appl. No. 17/051,585 mailed Mar. 29, 2023.
Non-Final Office Action for U.S. Appl. No. 17/051,600 mailed Jan. 17, 2024.
Non-Final Office Action for U.S. Appl. No. 17/179,116 mailed Feb. 26, 2024.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/378,015 mailed Jul. 5, 2024.
Non-Final Office Action for U.S. Appl. No. 17/444,792 mailed Feb. 10, 2023.
Non-Final Office Action for U.S. Appl. No. 17/444,792 mailed Nov. 17, 2023.
Non-Final Office Action for U.S. Appl. No. 17/446,256 mailed Apr. 13, 2023.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/446,654 mailed Sep. 8, 2023.
Non-Final Office Action for U.S. Appl. No. 17/447,123 mailed Jan. 24, 2024.
Non-Final Office Action for U.S. Appl. No. 17/448,811 mailed Jan. 17, 2024.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/450,864 mailed May 29, 2024.
Non-Final Office Action for U.S. Appl. No. 17/451,345 mailed Jan. 17, 2024.
Non-Final Office Action for U.S. Appl. No. 17/451,354 mailed Apr. 4, 2024.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/453,560 mailed Oct. 16, 2023.
Non-Final Office Action for U.S. Appl. No. 17/501,591 mailed Apr. 25, 2023.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/645,821 mailed Oct. 25, 2023.
Non-Final Office Action for U.S. Appl. No. 17/646,771 mailed Apr. 24, 2024.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/653,137 mailed Jan. 18, 2024.
Non-Final Office Action for U.S. Appl. No. 17/653,920 mailed Mar. 15, 2024.
Non-Final Office Action for U.S. Appl. No. 17/655,464 mailed Mar. 14, 2023.
Non-Final Office Action for U.S. Appl. No. 17/655,464 mailed Mar. 26, 2024.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/663,330 mailed Jun. 29, 2023.

(56) References Cited

OTHER PUBLICATIONS

Non-Final Office Action for U.S. Appl. No. 17/664,487 mailed Jun. 17, 2024.
Non-Final Office Action for U.S. Appl. No. 17/664,487 mailed Jun. 8, 2023.
Non-Final Office Action for U.S. Appl. No. 17/664,914 mailed Jan. 31, 2024.
Non-Final Office Action for U.S. Appl. No. 17/808,354 mailed Nov. 28, 2023.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Jun. 21, 2024.
Non-Final Office Action for U.S. Appl. No. 18/140,751 mailed Sep. 14, 2023.
Non-Final Office Action for U.S. Appl. No. 18/164,800 mailed Mar. 22, 2024.
Non-Final Office Action for U.S. Appl. No. 18/198,464 mailed Dec. 7, 2023.
Non-Final Office Action for U.S. Appl. No. 18/389,009 mailed May 24, 2024.
Notice of Allowance for U.S. Appl. No. 16/245,726 mailed Jul. 6, 2023.
Notice of Allowance for U.S. Appl. No. 16/369,676 mailed Jun. 17, 2024.
Notice of Allowance for U.S. Appl. No. 16/369,676 mailed Nov. 14, 2023.
Notice of Allowance for U.S. Appl. No. 16/449,039 mailed Mar. 28, 2024.
Notice of Allowance for U.S. Appl. No. 16/452,145 mailed Jul. 11, 2024.
Notice of Allowance for U.S. Appl. No. 17/051,550 mailed Feb. 7, 2024.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/326,980 mailed Apr. 5, 2024.
Notice of Allowance for U.S. Appl. No. 17/326,980 mailed Jan. 29, 2024.
Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jul. 28, 2023.
Notice of Allowance for U.S. Appl. No. 17/662,700 mailed Jun. 12, 2024.
Notice of Allowance for U.S. Appl. No. 17/662,700 mailed Mar. 28, 2023.
Notice of Allowance for U.S. Appl. No. 17/662,700 mailed Mar. 6, 2024.
Notice of Allowance for U.S. Appl. No. 17/662,700 mailed Nov. 15, 2023.
Notice of Allowance for U.S. Appl. No. 17/663,046 mailed Jan. 30, 2023.
Notice of Allowance for U.S. Appl. No. 18/198,464 mailed Apr. 17, 2024.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/527,769 mailed Jun. 17, 2024.
Restriction Requirement for U.S. Appl. No. 17/645,821 mailed Jul. 12, 2023.
Restriction Requirement for U.S. Appl. No. 17/646,771 mailed Apr. 6, 2023.
Restriction Requirement for U.S. Appl. No. 17/657,474 mailed Jun. 30, 2023.
Restriction Requirement for U.S. Appl. No. 17/667,097 mailed Mar. 20, 2024.
Restriction Requirement for U.S. Appl. No. 18/134,857 mailed Oct. 23, 2023.
Submission in Opposition Proceedings for European Application No. 17807547.9 filed Jan. 10, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
Text Messages to Lorena Eckert Re Prototype PureWick Holder dated Apr. 16, 2022.
U.S. Appl. No. 15/260,103, filed Sep. 8, 2016.
U.S. Appl. No. 15/612,325, filed Jun. 2, 2017.
U.S. Appl. No. 17/444,792, filed Aug. 10, 2021.
U.S. Appl. No. 17/451,719, filed Oct. 19, 2021.
U.S. Appl. No. 17/664,487, filed May 23, 2022.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/249,577, filed Oct. 19, 2021.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/294,370, filed Feb. 1, 2024.
U.S. Appl. No. 18/294,403, filed Feb. 1, 2024.
U.S. Appl. No. 18/299,788, filed Apr. 13, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/389,009, filed Nov. 13, 2023.
U.S. Appl. No. 18/415,080, filed Jan. 17, 2024.
U.S. Appl. No. 18/426,795, filed Jan. 30, 2024.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.

(56) References Cited

OTHER PUBLICATIONS

U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.
U.S. Appl. No. 18/569,778, filed Dec. 13, 2023.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/728,604, filed Jul. 12, 2024.
U.S. Appl. No. 18/757,964, filed Jun. 28, 2024.
U.S. Appl. No. 18/758,025, filed Jun. 28, 2024.
U.S. Appl. No. 63/150,640, filed Feb. 18, 2021.
U.S. Appl. No. 63/308,190, filed Feb. 9, 2022.
U.S. Appl. No. 63/561,893, filed Dec. 11, 2023.
U.S. Appl. No. 63/596,012, filed Nov. 3, 2023.
U.S. Appl. No. 63/608,553, filed Dec. 11, 2023.
*PureWick Corporation* v. *Sage Products, LLC* Transcripts vol. 2, Mar. 29, 2022.
*PureWick Corporation* v. *Sage Products, LLC* Transcripts vol. 3, Mar. 30, 2022.
*PureWick Corporation* v. *Sage Products, LLC* Transcripts vol. 4, Mar. 31, 2022.
*PureWick Corporation* v. *Sage Products, LLC* Transcripts vol. 5, Apr. 1, 2022.
*PureWick Corporation* v. *Sage Products, LLC* Transcripts vol. 1, Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
"AMXDmax Development History 2002-2014", Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.
"Letter to Mark Harvie of Omni Measurement Systems", Department of Veterans Affairs, Nov. 1, 2007, 11 pages.
"OBLONG", Cambridge Dictionary, https://dictionary.cambridge.org/dictionary/english/oblong, 2024, 1 page.
"Revised AMXDmax Advanced Mission Extender Device User & Maintenance Guide", Omni Medical Systems, Oct. 8, 2019, 52 pages.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Merriam-Webster Dictionary,, "Embed Definition & Meaning", https://www.merriam-webster.com/dictionary/embed last accessed Aug. 3, 2023, 2003.
Pieper, et al., "An external urine-collection device for women: A clinical trial", Journal of ER Nursing, vol. 20, No. 2, Mar./Apr. 1993, pp. 51-55.
Vinas, "A Solution For an Awkward—But Serious—Subject", http://www.aero-news.net/index.cfm?do=main.textpost&id=69ae2bb1-838b-4098-a7b5-7flbb2505688 last accessed Feb. 8, 2021.
Wikipedia Article, "Decibel" https://web.archive.org/web/20200415211917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Wikipedia Article, "Zylinder (Geometrie)", https://de.wikipedia.org/w/index.php?title=Zylinder (Geometrie)&oldid=154862081, version of Jun. 1, 2016, 7 pages.
Action for U.S. Appl. No. 14/722,613 mailed Mar. 4, 2019.
Action for U.S. Appl. No. 14/952,591 mailed Jun. 1, 2018.
Action for U.S. Appl. No. 15/238,427 mailed Apr. 10, 2019.
Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Corrected Notice of Allowability for U.S. Appl. No. 17/330,657 mailed Dec. 9, 2021.
Final Office Action for U.S. Appl. No. 14/722,613 mailed on Nov. 29, 2018.
Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/245,726 mailed Nov. 25, 2022.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/899,956 mailed Apr. 19, 2021.
Final Office Action for U.S. Appl. No. 16/904,868 mailed Mar. 10, 2022.
Final Office Action for U.S. Appl. No. 16/904,868 mailed Mar. 26, 2021.

(56) References Cited

OTHER PUBLICATIONS

Final Office Action for U.S. Appl. No. 16/905,400 mailed Apr. 6, 2021.
Final Office Action for U.S. Appl. No. 16/905,400 mailed Dec. 9, 2021.
Final Office Action for U.S. Appl. No. 17/088,272 mailed May 25, 2021.
Final Office Action for U.S. Appl. No. 17/662,700 mailed Sep. 30, 2022.
Final Office Action for U.S. Appl. No. 29/624,661 mailed Feb. 18, 2020.
International Search Report and Written Opinion from International Application No. PCT/IB2021/057173 mailed Nov. 5, 2021.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.

(56) References Cited

OTHER PUBLICATIONS

International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039714 mailed Nov. 22, 2022.
International Search Report and Written Opinion from International Application No. PCT/US2022/042719 mailed Dec. 5, 2022.
International Search Report and Written Opinion from International Application No. PCT/US2022/044107 mailed Dec. 23, 2022.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 29/624,661 mailed Aug. 4, 2021.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 malled Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 malled Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/051,550 mailed Dec. 15, 2022.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 17/451,345 mailed Dec. 7, 2022.
Non-Final Office Action for U.S. Appl. No. 17/662,700 mailed Jul. 22, 2022.
Non-Final Office Action for U.S. Appl. No. 29/624,661 mailed Jul. 18, 2019.

(56) References Cited

OTHER PUBLICATIONS

Non-Final Office Action for U.S. Appl. No. 29/694,002 mailed Jun. 24, 2020.
Non-Final Office Action for U.S. Appl. No. 29/741,751 mailed Jan. 18, 2022.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Oct. 6, 2022.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.
Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice of Allowance for U.S. Appl. No. 29/741,751 mailed Jun. 9, 2022.
Notice to File Missing Parts for U.S. Appl. No. 17/179,116 mailed Mar. 3, 2021.
Restriction Requirement for U.S. Appl. No. 16/433,773 mailed Dec. 7, 2021.
Restriction Requirement for U.S. Appl. No. 16/478,180 mailed May 25, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/384,196, filed Dec. 19, 2016.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585 filled Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591 filled Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697 filled Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.

(56) References Cited

OTHER PUBLICATIONS

U.S. Appl. No. 18/003,029, filed Dec. 22, 2022.
U.S. Appl. No. 18/006,807, filed Jan. 25, 2023.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 62/994,912, filed Mar. 26, 2020.
U.S. Appl. No. 63/008,112, filed Apr. 10, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657 filled Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032 filled Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261 filled Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
Sage's Second Supplemental Invalidity Contentions Regarding U.S. Pat. Nos. 8,287,508, 10,226,375, 10,390,989, and 10,376,407, 292 pages.
Plaintiff's Identification of Claim Terms and Proposed Constructions, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.

(56) References Cited

OTHER PUBLICATIONS

Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/US/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pil/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#IdivAbstract, 2015, 5 pages.
"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Rising Warrior Insulated Gallon Jug Cover", https://www.amazon.com/Rising-Warrior-Insulated-Sleeve, 2021, 2 pages.
"Step by Step How Ur24 WorksHome", http://medicalpatentur24.com, Aug. 30, 2017, 4 pages.
"Underwear that absorbs your period", Thinxl, 7 pages.
"Urine Bag Cover-Catheter Bag Cover 2000 ml vol. Medline Style-Multiple Sclerosis-Spine Injury-Suprapublic Catheter-Bladder Incontinence", https://www.etsy.com/listing/1142934658/urine-bag-cover-caatheter-bag-cover-2000, 2022, 1 page.
"User & Maintenance Guide", Omni Medical, 2007, 16 pages.
"Vinyl Dust Cover, Janome #741811000, Janome, Sewing Parts Online", https://www.sewingpartsonline.com/vinyl-dust-cover-janome-74181000, 2020, 2 pages.
"Winners Announced for Dare-to-Dream Medtech Design Challenge", https://www.mddionline.com/design-engineering/winners-announced-dare-dream-medtech-design-challenge, 2014, 4 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bloinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hollister , "Female Urinary and Pouch and Male Urinary Pouch Brochure", 2011, 1 page.
Hollister , "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister , "Retracted Penis Pouch by Hollister", Vitality Medical.com, 6 pages.
Hwang , et al., "Multifunctional Smart Skin Adhesive Patches for Advanced Health Care", Adv. Healthcare Mater, 2018, pp. 1-20.
Jagota , et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.
Lee , et al., "Continuous Fabrication of Wide-Tip Microstructures for Bio-Inspired Dry Adhesives via Tip Inking Process", Journal of Chemistry, Jan. 2, 2019, pp. 1-5.
Macaulay , et al., "A Noninvasive Continence Management System: Development and Evaluation of a Novel Toileting Device for Women", The Wound, Ostomy and Continence Nurses Society, 2007, pp. 641-648.
Newman , et al., "The Urinary Incontinence Sourcebook", Petition for Interparties Review, 1997, 23 pages.
Newton , et al., "Measuring Safety, Effectiveness and Ease of Use of PureWick in the Management of Urinary Incontinence in Bedbound Women: Case Studies", Jan. 8, 2016, 11 pages.
Parmar , "10 Finalists Chosen for Dare-to-Dream Medtech Design Challenge (PureWick)", Design Services, Nov. 10, 2014, 3 pages.
Parness , et al., "A microfabricated wedge-shaped adhesive array displaying gecko-like dynamic adhesion, directionality", J.R. Soc. Interface, 2009, pp. 1223-1232.
Purewick , "Incontinence Relief for Women", Presentation, Sep. 23, 2015, 7 pages.
Pytlik , "Super Absorbent Polymers", University of Buffalo.
Sachtman , "New Relief for Pilots? It Depends", Wired, 2008, 2 pages.
Tsipenyuk , et al., "Use of biomimetic hexagonal surface texture in friction against lubricated skin", Journal of the Royal Society—Interface, 2014, pp. 1-6.

* cited by examiner

FLUID COLLECTION SYSTEM INCLUDING A GARMENT AND A FLUID COLLECTION DEVICE

CROSS-REFERENCE TO RELATED APPLICATIONS

This application is a U.S. Nationalization of PCT International Application No. PCT/US2021/044699 filed on 5 Aug. 2021, which claims priority to U.S. Provisional Patent Application No. 63/061,834 filed on Aug. 6, 2020, the disclosure of which is incorporated herein, in its entirety, by this reference.

BACKGROUND

An individual may have limited or impaired mobility such that typical urination processes are challenging or impossible. For example, the individual may have surgery or a disability that impairs mobility. In another example, the individual may have restricted travel conditions such as those experienced by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, pressure ulcers spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are fluid collection systems and methods of use. In an embodiment, a fluid collection system includes a garment and fluid collection device. The garment is configured to be worn on a pelvis of a user. The garment includes at least a crotch portion having an inner surface and at least one of a strap partially defining a through hole between the strap and the inner surface or a pocket on the inner surface of the crotch portion. The fluid collection device has at least a portion sized and shaped to fit within one or more of the at least one of the through hold or the pocket. The fluid collection device including a fluid impermeable barrier and a fluid permeable body. The fluid impermeable barrier at least partially defines a chamber, an opening extending longitudinally along the fluid impermeable barrier and configured to be positioned adjacent to a urethra of the user, and an aperture configured to receive a conduit therethrough. The fluid permeable body is positioned at least partially within the chamber to extend across at least a portion of the opening and configured to wick fluid away from the opening. The at least one of the strap or the pocket are positioned on the crotch portion of the garment and the fluid collection device is sized to position the opening and the fluid permeable body at least proximate to the urethra of the user.

In an embodiment, a fluid collection system includes a garment, a fluid collection device, and a conduit. The garment is configured to be worn on a pelvis of a user. The garment includes at least a crotch portion having an inner surface and a strap secured to the inner surface of the garment and at least partially defining a through hole between the strap and the inner surface. The fluid collection device includes a fluid impermeable barrier and a fluid permeable body. The fluid impermeable barrier at least partially defines a chamber, an opening extending longitudinally along the fluid impermeable barrier and configured to be positioned adjacent to a urethra of the user, and an aperture configured to receive a conduit therethrough. The fluid permeable body is positioned at least partially within the chamber to extend across at least a portion of the opening and configured to wick fluid away from the opening. The conduit extends through the aperture such that a first portion of the conduit is disposed within the chamber and a second portion of the conduit is disposed outside the chamber. The conduit has at least a portion sized and shaped to fit within the through hole. The strap is positioned on the crotch portion of the garment and the fluid collection device is sized to position the opening and the fluid permeable body at least proximate to the urethra of the user.

In an embodiment, a method of collecting fluid includes securing a fluid collection device to an inner surface of a garment. The fluid collection device is secured to the inner surface of the garment by at least one of securing a first end region of a fluid impermeable barrier of the fluid collection device in a through hole defined by a portion of the inner surface and a strap secured to the inner surface, or inserting a second end region of the fluid impermeable barrier of the fluid collection device in a pocket on the inner surface of the pocket. The method also includes disposing the garment on the wearer such that an opening in the fluid impermeable barrier and a fluid permeable body disposed in a chamber defined by the fluid impermeable body are positioned adjacent to the urethra of the wearer. The method also includes receiving fluids from the urethra into the chamber.

In an embodiment, a garment configured to be worn on a pelvis of a user to collect fluid includes a waistband and at least a portion having an inner surface. The crotch portion also includes at least one of a strap or a pocket. The strap partially defines a through hole between the strap and the inner surface, the through hole being sized and dimensioned to secure a conduit or a first end region of a fluid impermeable barrier of a fluid collection device therein. The pocket is on the inner surface of the crotch portion and is sized and dimensioned to secure the second end region of a fluid impermeable barrier of the fluid collection device therein. The at least one of the strap or the pocket are positioned on the inner surface of the crotch portion to position an opening and a fluid permeable body of the fluid collection device at least proximate to a urethra of the user when the fluid collection device is secured to the inner surface with the at least one of the strap or the pocket.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Figure 1:
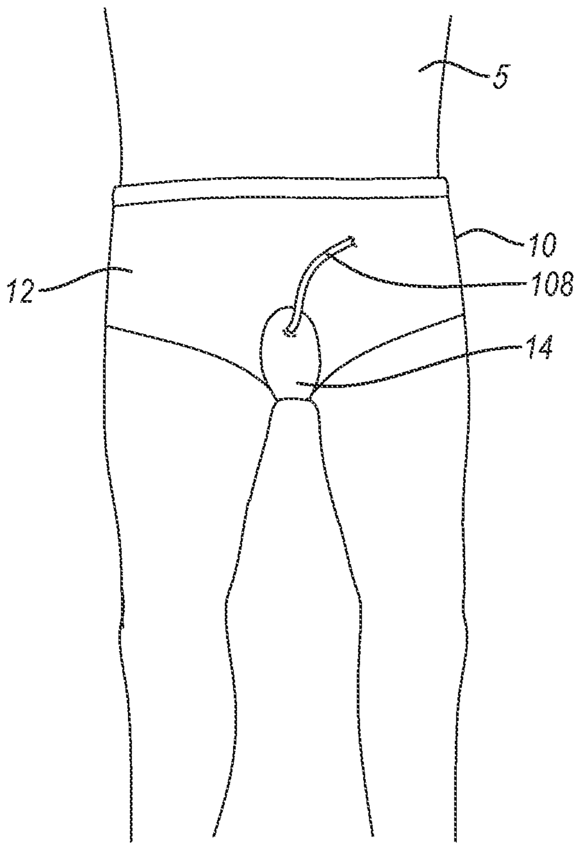
FIG. 1 is a front view of a garment for fluid collection worn on a user, according to an embodiment.

Embodiments disclosed herein are related to garments carrying fluid collection devices and methods of using the same. The garments may include one or more of breathable materials and/or absorptive materials. The garments include a crotch portion having one or more securement features providing the technical effect of securing a fluid collection device on an inner surface of the crotch portion. The one or more securement features can include various combinations of one or more straps and a pocket configured to allow a user to secure the fluid collection device to the crotch portion of the garment, as well as remove the fluid collection device from the crotch portion. For example, the one or more securement features may include a strap configured to secure a conduit to the inner surface of the crotch portion, a strap configured to secure a proximate or first end region of the fluid impermeable barrier of the fluid collection device to the inner surface of the crotch portion, and/or a pocket configured to secure a distal or second end region of the fluid impermeable barrier to the inner surface of the crotch portion. The securement features and the crotch portion of the garment provide the technical effect of aligning the fluid collection device thereon with one or more anatomical structures (e.g., urethra) of the wearer when the garment is worn.

The fluid collection devices include a fluid impermeable barrier that at least partially defines a chamber therein. The fluid impermeable barrier also defines an opening extending therethrough that is configured to be positioned adjacent to a female urethra or have a male urethra positioned therethrough. In some examples, the garment results in the technical effect of positioning the opening in the fluid impermeable barrier and the fluid permeable body adjacent the urethra and/or next to the skin surround the urethral opening. The fluid collection device includes a conduit for removing fluid from the chamber. The conduit includes an inlet in fluid communication with (e.g., positioned within) the chamber of the fluid collection device and an outlet configured to be in fluid communication with (e.g., fluidly coupled to) a vacuum source or fluid storage container. The fluid collection device also include a tube having a channel extending between an inlet and outlet thereof. The inlet is configured to be in fluid communication with the vacuum source and the outlet is configured to be in fluid communication with a fluid storage (vessel or container), or vice versa. The outlet is positioned downstream from the inlet.

The garments disclosed herein are configured to collect fluids from an individual. The fluids collected by the garments (e.g., via fluid collection devices positioned therein and/or secured thereto) can include urine. The fluids collected by the fluid collection devices can also include at least one of vaginal discharge, penile discharge, reproductive fluids, blood, sweat, or other bodily fluids. The fluid collection garments, systems, and methods disclosed herein can help keep a wearer dry and sanitary while reducing or eliminating the need for more invasive means of collecting fluid emissions such as catheterization.

FIG. 1 is a front view of a garment 10 for fluid collection, according to an embodiment. The garment 10 includes a fabric body 12 that is sized and shaped to fit on a pelvis of a wearer or user 5 and maintain position thereon. The garment 10 also includes a crotch portion 14 therein. The crotch portion 14 may be positioned in the crotch of the garment 10 (e.g., a position corresponding to the crotch of the user 5 when the garment 10 is worn). The crotch portion 14 of the garment can include the region of the garment positioned to cover an area extending from the pubic region to the anus or the perineum of the subject when the garment is worn. The crotch portion 14 is positioned over at least the region of the urethra of the user 5 (e.g., within the region of the crotch) when the garment 10 is worn. A fluid collection device (not shown) may be disposed on an inner surface of the crotch portion (described in greater detail below), such that fluids in the region, such as urine, may be collected by the fluid collection device. Accordingly, the garment 10 may provide the technical effect of aligning the fluid collection device with the urethra of the user such that fluids originating therefrom can be collected before soiling clothing or bedding. The garment 10 also includes one or more (e.g., two) leg openings and a waist opening.

The fabric body 12 and/or the crotch portion 14 may include one or more of natural materials such as cotton, wool, silk, rubber, etc. or synthetic materials such as polyamides (e.g., NYLON), poly(ethylene terephthalate), beta-1,4-Glucan-4-Glucanohydrolase (e.g., Rayon), polyester, silicone, a polyether-polyurea copolymer (e.g., SPANDEX), olefin fibers, acrylic fibers, etc. The fabric body 12 and/or the crotch portion 14 may include one or more breathable material and/or one or more absorptive materials. In some examples, at least one of the fabric body 12 and/or the crotch portion 14 include one or more of a mesh fabric, a woven fabric, or a non-woven material. In some embodiments, the fabric body 12 and the crotch portion 14 of the undergarment 10 may include identical material(s). In some embodiments, the fabric body 12 and the crotch portion 14 may include one or more different materials. For example, the undergarment 10 can include one or more portions which include a relatively soft fabric and one or more portions that include a relatively rough fabric. In some examples, the undergarment 10 can include a cotton gusset crotch portion 14 and a nylon body 12. In some examples, the fabric body 12 may include materials configured for user comfort, such as cotton, wool, silk, or synthetic materials such as polyamides (e.g., NYLON), poly(ethylene terephthalate), beta-1,4-Glucan-4-Glucanohydrolase (e.g., Rayon), polyester, silicone, a polyether-polyurea copolymer (e.g., SPANDEX), olefin fibers, acrylic fibers, etc. The crotch portion 14 may include materials configured to absorb fluids or wick fluids away from the skin of the user 5. For example, the crotch portion 14 may consist of or consist essentially of a mesh, a porous, and/or fibrous material, such as hydrophilic polyolefin.

Examples of polyolefin that may be used in the crotch portion 14 include, but are not limited to, polyethylene, polypropylene, polyisobutylene, ethylene propylene rubber, ethylene propylene diene monomer, or combinations thereof.

The garment 10 can be shaped as a variety of garments, such as an undergarment, pants, shorts, a jock-strap, adjustable versions of any of the foregoing, or analogues of any of the foregoing. In such examples, stitching, buttons, snaps, or other fasteners can join a plurality of panels which collectively form the garment.

The crotch portion 14 may be positioned on the undergarment 10 such that the crotch portion 14 is located about a urethral region on the pelvis of the user 5 when the garment 10 is worn. For example, the crotch portion 14 can be positioned over or in the crotch of the undergarment 10. The crotch portion 14 can provide the technical effect of securing and retaining a fluid collection device in place over the urethral region on the pelvis of the user 5. The crotch portion 14 may be sown on or in the fabric body 12. The crotch portion 14 may be integrally formed in the fabric body 12 (e.g., weaved into the fabric body 12).

The crotch portion 14 may be releasably and selectively attachable to the fabric body 12. For example, the crotch portion 14 may be affixed to the fabric body by hook and loop fasteners, buttons, snaps, a zipper, magnets, or any other fastener. In such examples, the fabric body 12 can include a male portion of the snap connection, a hook strip, a button, or a magnet disposed in the region around the crotch of the subject, such as around the periphery of the region where a urethra of a wearer may be located while the garment is worn. The piece of fabric defining the crotch portion 14 can include a female portion of the snap connection, a loop strip, a button-hole, or a magnet disposed about a periphery of the piece of fabric. In such examples, the crotch portion 14 can be aligned and retained on the fabric body 12 by the snap connection, hook strip, button, or magnet. Accordingly, the garment 10 can provide a technical effect of a crotch portion 14 that is removable and replaceable, such as to insert, replace, clean, or otherwise service the fluid collection device in the garment 14. Furthermore, the garment 10 can provide a technical effect of a crotch portion 14 that allows removal and replacement of a fluid collection device without removing the garment 10.

Figure 2A:
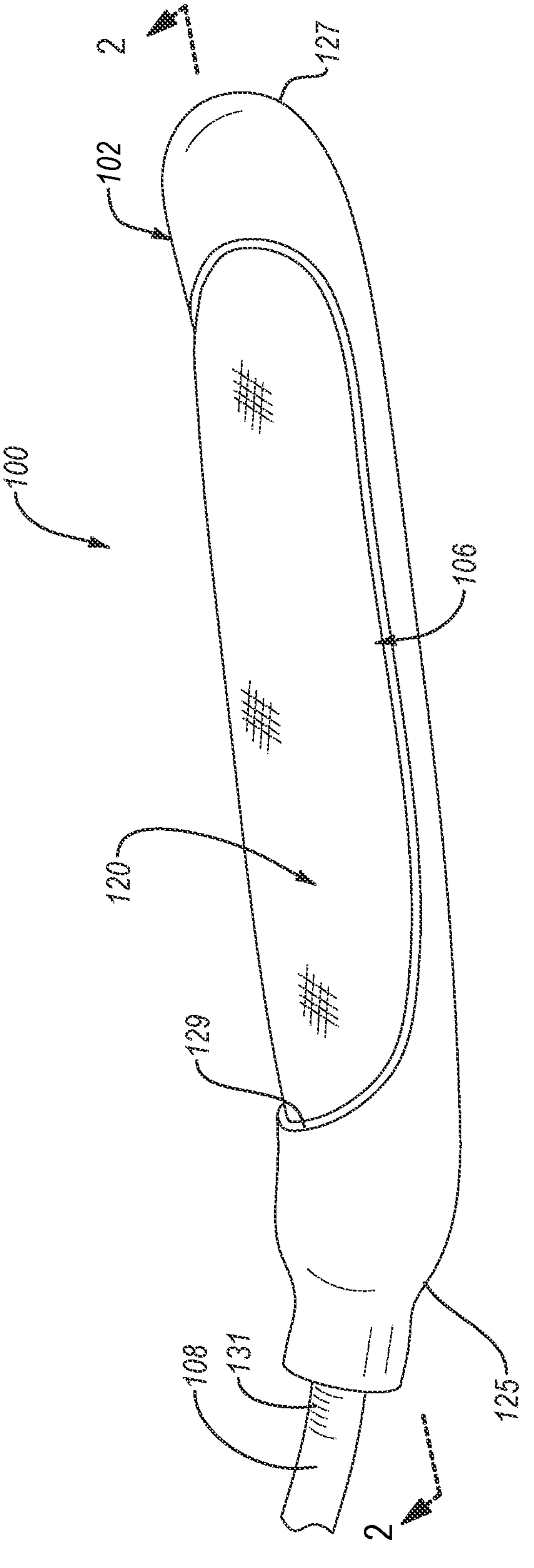
FIG. 2A is an isometric view of a fluid collection device, according to an embodiment.

A fluid collection device can be secured the garment 10 (e.g., on the crotch portion 14). For example, the crotch portion 14 may be sized and shaped to accommodate a female fluid collection device or a male fluid collection device, such as any of those disclosed herein. FIG. 2A is an isometric view of a fluid collection device 100, according to an embodiment. The fluid collection device 100 is an example of a female fluid collection device 100 that is configured to receive fluids from a female. The fluid collection device 100 includes a fluid impermeable barrier 102 having a first end region 125 and a second end region 127. The fluid impermeable barrier 102 at least partially defines a chamber 104 (e.g., interior region, shown in FIG. 2C) and includes an inward border or edge 129 defining an opening 106. The fluid impermeable barrier 102 is substantially cylindrical in shape between the first end region 125 and the second end region 127. In other embodiments, the fluid impermeable barrier 102 may include other shapes, such as one of more substantially planar surfaces, triangular, or other suitable shape. The opening 106 is formed in and extends longitudinally through the fluid impermeable barrier 102, thereby enabling fluids to enter the chamber 104 from outside of the fluid collection device 100. The opening 106 may be configured to be positioned adjacent to the opening of a female urethra.

The fluid collection device 100 may be positioned at least proximate to the opening of the female urethra and urine may enter the interior region of the fluid collection device 100 via the opening 106. The fluid collection device 100 is configured to receive the fluids into the chamber 104 via the opening 106. For example, the opening 106 may exhibit an elongated shape that is configured to extend from a first location below the urethral opening (e.g., at or near the anus or the vaginal opening) to a second location above the urethral opening (e.g., at or near the clitoris or the pubic hair). The opening 106 may exhibit an elongated shape since the space between the legs of a female is relatively small when the legs of the female are closed, thereby only permitting the flow of the fluids along a path that corresponds to the elongated shape of the opening 106. For example, the opening may extend longitudinally along the fluid impermeable barrier. The opening 106 in the fluid impermeable barrier 102 may exhibit a width that is measured transverse to the longitudinal direction and may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 may exhibit a width that is greater than 50% of the circumference of the fluid collection device 100 since the vacuum (e.g., suction) through the conduit 108 pulls the fluid into the conduit 108. In some embodiments, the opening 106 may be vertically oriented (e.g., having a major axis parallel to the longitudinal axis of the device 100). In some embodiments, (not shown), the opening 106 may be horizontally oriented (e.g., having a major axis perpendicular to the longitudinal axis of the device 100). In some embodiments, the inward border or edge 129 of the fluid impermeable barrier 102 defines the opening 106. The edge 129 may include two opposing arced portions, the arc portions following the outer circumference or periphery of the substantially cylindrical fluid impermeable barrier 102. In an embodiment, the fluid impermeable barrier 102 may be configured to be attached to the individual, such as adhesively attached (e.g., with a hydrogel adhesive) to the individual. According to an embodiment, a suitable adhesive is a hydrogel layer, such as those disclosed in U.S. Patent Application Publication No. 2017/0189225, the disclosure of which is incorporated herein by reference in its entirety.

The fluid impermeable barrier 102 may also temporarily store the fluids in the chamber 104. For example, the fluid impermeable barrier 102 may be formed of any suitable fluid impermeable materials, such as a fluid impermeable polymer (e.g., silicone, polypropylene, polyethylene, polyethylene terephthalate, a polycarbonate, etc.), polyurethane films, thermoplastic elastomer (TPE), rubber, thermoplastic polyurethane, another suitable material, or combinations thereof. As such, the fluid impermeable barrier 102 substantially prevents the fluids from exiting the portions of the chamber 104 that are spaced from the opening 106. The fluid impermeable barrier 102 is flexible, thereby enabling the fluid collection device 100 to bend or curve when positioned against the body of a wearer. Example fluid impermeable barriers may include, but are not limited to, a fluid impermeable barrier including at least one of Versaflex CL 2000X TPE, Dynaflex G6713 TPE, or Silpuran 6000/05 A/B silicone.

In an embodiment, the fluid impermeable barrier 102 may be air permeable. In such an embodiment, the fluid impermeable barrier 102 may be formed of a hydrophobic material that defines a plurality of pores. In an embodiment, one or more portions of at least the outer surface of the fluid impermeable barrier 102 may be formed from a soft and/or smooth material, thereby reducing chaffing. The fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of alignment guide or an orientation indicator, such as a stripe or hashes. Such markings may be positioned to align the device 100 to one or more anatomical features such as a pubic bone, etc.

The fluid collection device 100 may include a fluid permeable body 120 or layer disposed in the chamber 104. The fluid permeable body 120 may cover or extend across at least a portion (e.g., all) of the opening 106. The fluid permeable body 120 may be configured to wick any fluid away from the opening 106, thereby preventing the fluid from escaping the chamber 104. The fluid permeable body 120 also may wick the fluid generally towards an interior of the chamber 104, as discussed in more detail below. A portion of the fluid permeable body 120 may define a portion of an outer surface of the fluid collection device 100. Specifically, the portion of the fluid permeable body 120 defining the portion of the outer surface of the fluid collection device 100 may be the portion of the fluid permeable body 120 exposed by the opening 106 defined by the fluid impermeable barrier 102 that contacts the user. Moreover, the portion of the fluid permeable device defining the portion of the outer surface of the fluid collection device 100 may be free from coverage by gauze or other wicking material at the opening.

The fluid permeable body 120 may include any material that may wick the fluid. The permeable properties referred to herein may be wicking, capillary action, diffusion, or other similar properties or processes, and are referred to herein as "permeable" and/or "wicking." Such "wicking" may exclude absorption into the wicking material. The fluid permeable body 120 may include a one-way fluid movement fabric. As such, the fluid permeable body 120 may remove fluid from the area around the female urethra, thereby leaving the urethra dry. The fluid permeable body 120 may enable the fluid to flow generally towards a reservoir 122 (shown in FIGS. 2B and 2C) of void space formed within the chamber 104. For example, the fluid permeable body 120 may include a porous or fibrous material, such as hydrophilic polyolefin. In some embodiments, the fluid permeable body 120 consists of or consists essentially of a porous or fibrous material, such as hydrophilic polyolefin. Examples of polyolefin that may be used in the fluid permeable body 120 include, but are not limited to, polyethylene, polypropylene, polyisobutylene, ethylene propylene rubber, ethylene propylene diene monomer, or combinations thereof. The porous or fibrous material may be extruded into a substantially cylindrically shape to fit within the chamber 104 of the fluid impermeable barrier 102. The fluid permeable body 120 may include varying densities or dimensions. Moreover, the fluid permeable body 120 may be manufactured according to various manufacturing methods, such as molding, extrusion, or sintering.

In some embodiments, the fluid permeable body 120 includes a singular and porous body. That is, during use, the fluid permeable body 120 extends from the conduit 108 to interface the fluid impermeable barrier 102 and the opening 106. In some embodiments, a majority of the outer surface 109 (shown in FIG. 2D) of the fluid permeable body 120 interfaces with an inner surface 103 (shown in FIG. 2D) of the fluid impermeable barrier 106. A singular fluid permeable body 120 may be advantageous to conventional systems, which typically require an air-laid nonwoven pad covered by a ribbed fabric compression bandage, because a singular fluid permeable body 120 reduced the number of components in the fluid collection device 100, reduces the assembly time of the fluid collection device 100, requires shelf-life data for only a single component, and provides a latex-free single component. In some embodiments, at least a portion of the singular porous material of the fluid permeable body 120 extends continuously between the opening 106 and the reservoir 122 to wick any fluid from the opening 106 directly to the reservoir 122. Moreover, as the fluid impermeable barrier 102 is flexible and the fluid permeable body 120 is configured to wick fluid from the body rather than absorb fluid from the body and hold the fluid against the body, the fluid collection device 100, in some embodiments, is free from a seal or cushioning ring on the inward edge 129 defining the opening 106. In these and other embodiments, the fluid permeable body 120 includes an outer surface and a single layer or type of material between the opening 106 and the conduit 108 positioned within the fluid permeable body 120.

In other embodiments, the fluid permeable body 120 may include two or more layers of fluid permeable materials and include no (or an absence of) more than two layers of material between the opening 106 and the conduit 108 positioned within the fluid permeable body 120. For example, the fluid collection device 100 may include a fluid permeable membrane covering or wrapping around at least a portion of a fluid permeable body, with both the fluid permeable membrane and the fluid permeable body being disposed in the chamber 104. The fluid permeable membrane may cover or extend across at least a portion (e.g., all) of the opening 106. The fluid permeable membrane may be configured to wick any fluid away from the opening 106, thereby preventing the fluid from escaping the chamber 104. The permeable properties referred to herein may be wicking, capillary action, diffusion, or other similar properties or processes, and are referred to herein as "permeable" and/or "wicking." In some embodiments, at least one of the fluid permeable membrane or the fluid permeable support include nylon configured to wick fluid away from the opening 106. The material of the fluid permeable membrane and the fluid permeable support also may include natural fibers. In such examples, the material may have a coating to prevent or limit absorption of fluid into the material, such as a water repellent coating. Such "wicking" may not include absorption into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the wicking material (e.g., absorbency), such as about 30 wt % of the dry weight of the wicking material, about 20 wt %, about 10 wt %, about 7 wt %, about 5 wt %, about 3 wt %, about 2 wt %, about 1 wt %, or about 0.5 wt % of the dry weight of the wicking material.

The fluid permeable membrane may also wick the fluid generally towards an interior of the chamber 104, as discussed in more detail below. The fluid permeable membrane may include any material that may wick the fluid. For example, the fluid permeable membrane may include fabric, such as a gauze (e.g., a silk, linen, polymer based materials such as polyester, or cotton gauze), another soft fabric (e.g., jersey knit fabric or the like), or another smooth fabric (e.g., rayon, satin, or the like). Forming the fluid permeable membrane from gauze, soft fabric, and/or smooth fabric may reduce chaffing caused by the fluid collection device 100. Other embodiments of fluid permeable membranes, fluid permeable supports, chambers, and their shapes and configurations are disclosed in U.S. patent application Ser. No. 15/612,325 filed on Jun. 2, 2017; U.S. patent application Ser. No. 15/260,103 filed on Sep. 8, 2016; U.S. patent application Ser. No. 15/611,587 filed on Jun. 1, 2017; PCT Patent Application No. PCT/US19/29608, filed on Apr. 29, 2019, the disclosure of each of which is incorporated herein, in its entirety, by this reference. In many embodiments, the fluid permeable body 120 includes a fluid permeable support including a porous nylon structure (e.g., spun nylon fibers) and a fluid permeable membrane including gauze about or over the porous nylon structure.

In use, the fluid permeable body 120 of the fluid collection device is positioned adjacent to a urethra of the user 150. The fluid permeable body 120 is disposed within a chamber 104 (shown in FIGS. 2B and 2C) of the fluid impermeable barrier 102 of the fluid collection device 100 and is exposed to the urethra of the user 150 through the opening 106 in the fluid collection device 100. The fluid collection device 100 may be secured to the user with any of a number of securing devices. Fluids received in the chamber 104 of the fluid collection device 100 from the urethra may be removed through the conduit 108.

Figure 2B:
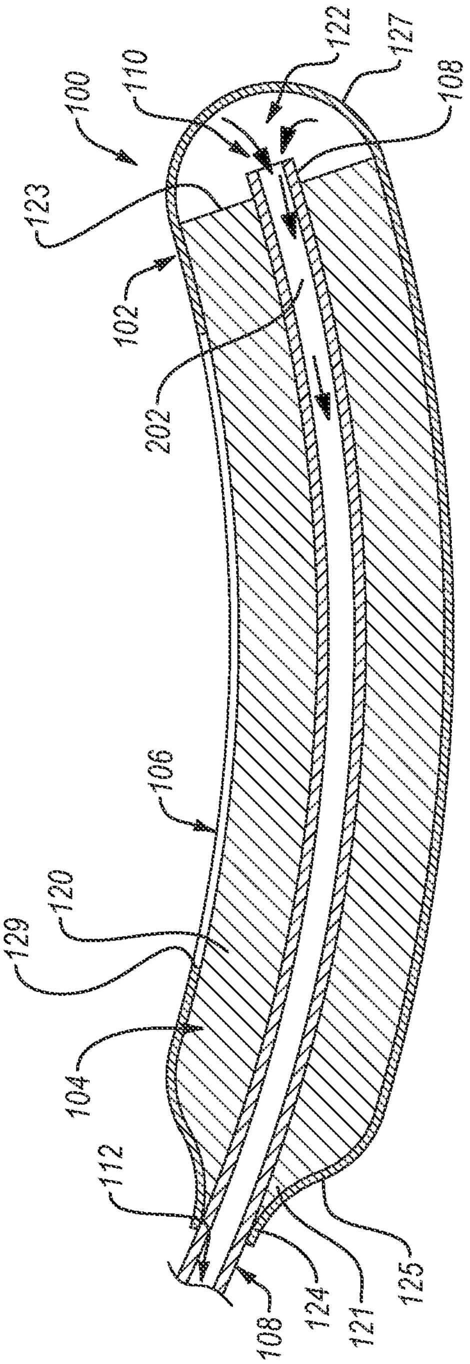
FIGS. 2B and 2C are cross-sectional views of the female fluid collection device of FIG. 1 taken along line 2-2 thereof, according to various embodiments.

FIG. 2B is a cross-sectional view of the fluid collection device 100 taken along line 2-2 of FIG. 2A. The fluid collection device 100 also includes conduit 108 that is at least partially disposed in the chamber 104. The conduit 108 (e.g., a tube) includes an inlet 110 at a second end region 127 of the fluid impermeable barrier 102 and an outlet 112 at a first end region 125 of the fluid impermeable barrier 102 positioned downstream from the inlet 110. The conduit 108 provides fluid communication between an interior region of the chamber 104 and a fluid storage container (not shown) or a portable vacuum source (not shown). For example, the conduit 108 may directly or indirectly fluidly couple the interior region of the chamber 104 and/or the reservoir 122 with the fluid storage container or the portable vacuum source.

In the illustrated embodiment, the fluid permeable body 120 defines a bore 202 extending through the fluid permeable body 120 from a first body end 121 of the fluid permeable body 120 to a second body end 123 of the fluid permeable body 120 distal to the first body end 120. In other embodiments, the bore 202 extends only partially into the fluid permeable body from the first body end 121 of the fluid permeable body 120.

In the illustrated embodiment, the conduit 108 is at least partially disposed in the chamber 104 and interfaces at least a portion of the bore 202 of the fluid permeable body 120. For example, the conduit 108 may extend into the fluid impermeable barrier 102 from the first end region 125 (e.g., proximate to the outlet 112) and may extend through the bore 202 to the second end region 127 (e.g., opposite the first end region 125) to a point proximate to the reservoir 122 such that the inlet 110 is in fluid communication with the reservoir 122. For example, in the illustrated embodiment, the inlet 110 is positioned in the reservoir 122. However, in other embodiments, the inlet 110 may be positioned flush with or behind an end of the fluid permeable body 120 that partially defines the reservoir 122. The fluid collected in the fluid collection device 100 may be removed from the interior region of the chamber 104 via the conduit 108. The conduit 108 may include a flexible material such as plastic tubing (e.g., medical tubing). Such plastic tubing may include a thermoplastic elastomer, polyvinyl chloride, ethylene vinyl acetate, polytetrafluoroethylene, etc., tubing. In some embodiments, the conduit 108 may include silicone or latex.

The fluid impermeable barrier 102 may store fluids in the reservoir 122 therein. The reservoir 122 is an unoccupied portion of the chamber 104 and is void of other material. In some embodiments, the reservoir 122 is defined at least partially by the fluid permeable body 120 and the fluid impermeable barrier 102. For example, in an embodiment, the reservoir 122 may be located at the portion of the chamber 104 that is closest to the inlet 110 (e.g., the second end region). Accordingly, in the embodiment in FIG. 2B, the reservoir 122 is defined by the second body end 123 of the fluid permeable body 120 and the second end region 127 of the fluid impermeable barrier 122. However, the reservoir 122 may be located at different locations in the chamber 104. For example, the reservoir 122 may be located at the end of the chamber 104 that is closest to the outlet 112. In these and other embodiments, the conduit 108 may extend through the first end region 125 of the fluid impermeable barrier 102 and to the reservoir 122 without extending through the fluid permeable body 120. Accordingly, in these and other embodiments, the fluid permeable body 120 may be free from the bore. In another embodiment, the fluid collection device 100 may include multiple reservoirs, such as a first reservoir that is located at the portion of the chamber of the chamber 104 that is closest to the inlet 110 (e.g., second end region) and a second reservoir that is located at the portion of the of the chamber 104 that is closest to the outlet 112 (e.g., first end region). In another example, the fluid permeable body 120 is spaced from at least a portion of the conduit 108 and the reservoir 122 may be the space between the fluid permeable body 120 and the conduit 108. Other embodiments of reservoirs, fluid impermeable barriers, fluid permeable membranes, fluid permeable bodies, chambers, and their shapes and configurations are disclosed in U.S. patent application Ser. No. 15/612,325 filed on Jun. 2, 2017; U.S. patent application Ser. No. 15/260,103 filed on Sep. 8, 2016; and U.S. patent application Ser. No. 15/611,587 filed on Jun. 1, 2017, the disclosure of each of which is incorporated herein, in its entirety, by this reference.

The fluid impermeable barrier 102 and the fluid permeable body 120 may be configured to have the conduit 108 at least partially disposed in the chamber 104. For example, the fluid permeable body 120 may be configured to form a space that accommodates the conduit 108, such as the bore 202. In another example, the fluid impermeable barrier 102 may define an aperture 124 sized to receive the conduit 108 (e.g., at least one tube). The at least one conduit 108 may be disposed in the chamber 104 via the aperture 124. The aperture 124 may be configured to form an at least substantially fluid tight seal against the conduit 108 or the at least one tube thereby substantially preventing the fluids from escaping the chamber 104.

Figure 2C:
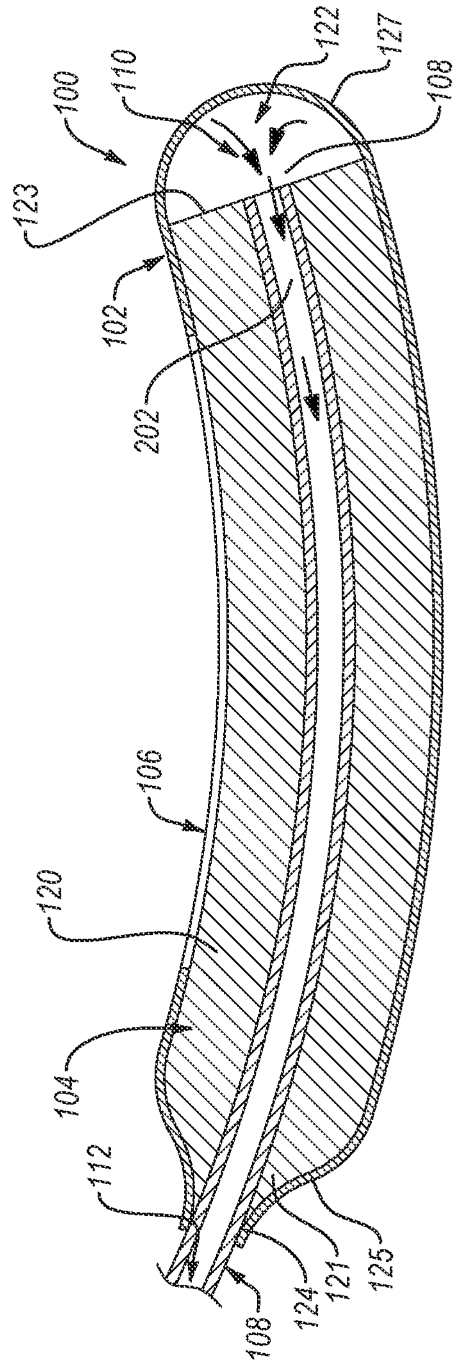
Figure 2D:
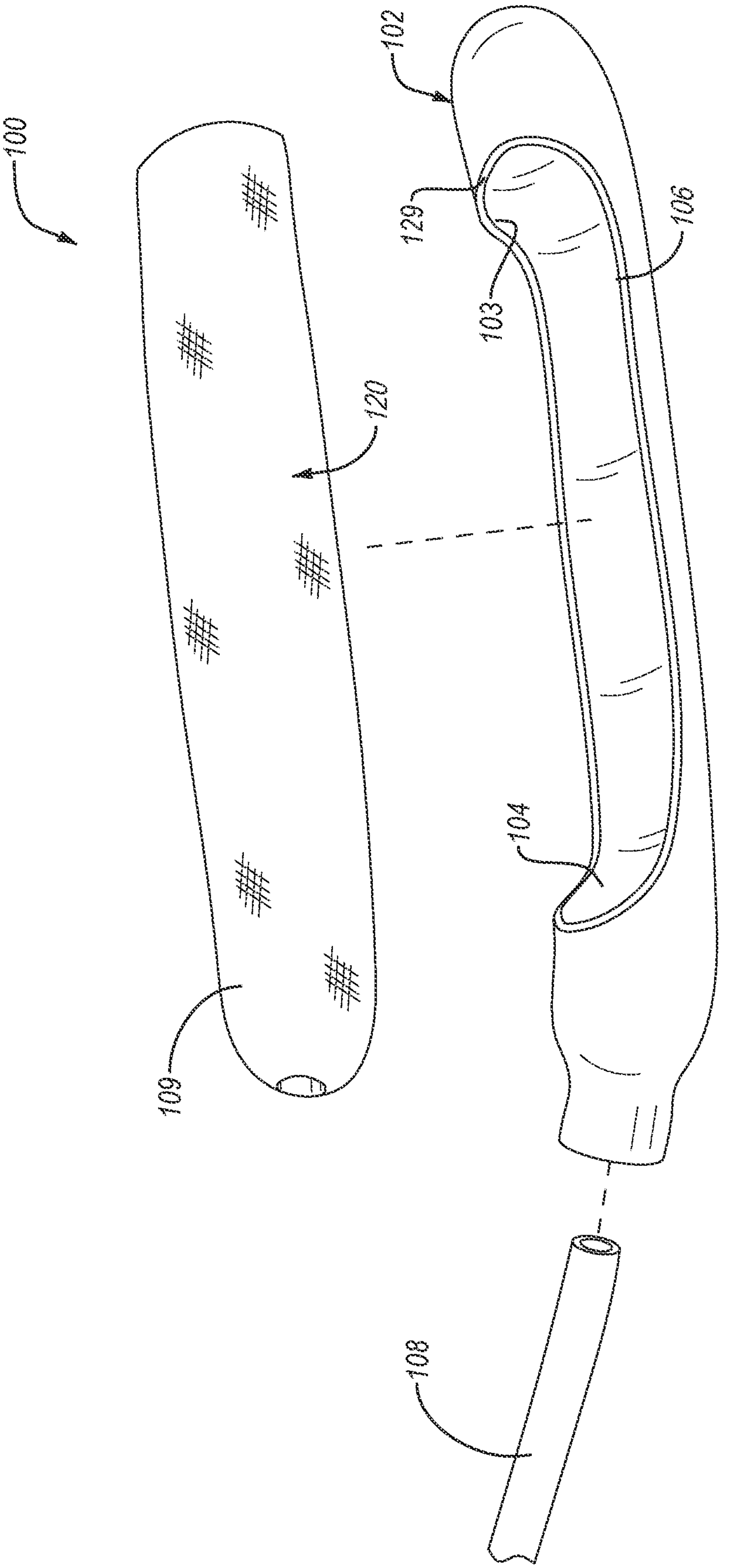
FIG. 2D is an exploded view of the female fluid collection device of FIG. 2A.

In some embodiments, the conduit 108 may extend through the fluid permeable body 120 and at least partially into the reservoir 122, as shown in FIG. 2B. In some embodiments, the conduit 108 may extend through the fluid permeable body 120 and terminate at or before the second body end 123 of the fluid permeable body 120 such that the conduit 108 does not extend into the reservoir 122 (or the reservoir 122 is absent of the conduit 108). For example, as shown in FIG. 2C, an end of the conduit 108 may be generally flush or coplanar with the second body end 123 of the fluid permeable body 120. In other embodiments, the end of the conduit 108 may be recessed from the second body end 123 of the fluid permeable body 120. The end of the conduit 108 also may be selectively moveable between partially extending into the reservoir 122 (shown in FIG. 2B) and recessed from or flush with the second body end 123 of the fluid permeable body (shown in FIG. 2C).

When secured to the fluid collection device 100, the conduit 108 is configured to provide fluid communication with and at least partially extend between one or more of a fluid storage containers (not shown) and a portable vacuum source (not shown). For example, the conduit 108 may be configured to be fluidly coupled to and at least partially extend between one or more of the fluid storage containers and the portable vacuum source. In an embodiment, the conduit 108 is configured to be directly connected to the portable vacuum source (not shown). In such an example, the conduit 108 may extend from the fluid impermeable barrier 102 by at least one foot, at least two feet, at least three feet, or at least six feet. In another example, the conduit 108 is configured to be indirectly connected to at least one of the fluid storage container (not shown) or the portable vacuum source (not shown). In some examples, the conduit may be frosted or opaque (e.g., black) to obscure visibility of the fluids therein. In some embodiments, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211,063, the disclosures of which are all incorporated herein by reference in their entirety.

The inlet 110 and the outlet 112 are configured to provide fluid communication (e.g., directly or indirectly) between the portable vacuum source (not shown) and the chamber 104 (e.g., the reservoir 122). For example, the inlet 110 and the outlet 112 of the conduit 108 may be configured to directly or indirectly fluidly couple the portable vacuum source to the reservoir 122. In an embodiment, the inlet 110 and/or the outlet 112 may form a male connector. In another example, the inlet 110 and/or the outlet 112 may form a female connector. In an embodiment, the inlet 110 and/or the outlet 112 may include ribs that are configured to facilitate secure couplings. In an embodiment, the inlet 110 and/or the outlet 112 may form a tapered shape. In an embodiment, the inlet 110 and/or the outlet 112 may include a rigid or flexible material.

Locating the inlet 110 at or near a gravimetrically low point of the chamber 104 enables the conduit to receive more of the fluids than if inlet 110 was located elsewhere and reduce the likelihood of pooling (e.g., pooling of the fluids may cause microbe growth and foul odors). For instance, the fluids in the fluid permeable body 120 may flow in any direction due to capillary forces. However, the fluids may exhibit a preference to flow in the direction of gravity, especially when at least a portion of the fluid permeable body 120 is saturated with the fluids.

As the portable vacuum source applies a vacuum/suction in the conduit 108, the fluid(s) in the chamber 104 (e.g., such as in the reservoir 122 positioned at the first end region 125, the second end region 127, or other intermediary positions within the chamber 104) may be drawn into the inlet 110 and out of the fluid collection device 100 via the conduit 108.

In an embodiment, the conduit 108 is configured to be at least insertable into the chamber 104. In such an embodiment, the conduit 108 may include one or more markers 131 (shown in FIG. 2A) on an exterior thereof that are configured to facilitate insertion of the conduit 108 into the chamber 104. For example, the conduit 108 may include one or more markings thereon that are configured to prevent over or under insertion of the conduit 108, such as when the conduit 108 defines an inlet 110 that is configured to be disposed in or adjacent to the reservoir 122. In another embodiment, the conduit 108 may include one or more markings thereon that are configured to facilitate correct rotation of the conduit 108 relative to the chamber 104. In an embodiment, the one or more markings may include a line, a dot, a sticker, or any other suitable marking. In examples, the conduit 108 may extend into the fluid impermeable barrier 102 from the first end region (e.g., proximate to the outlet 112) and may extend to the second end region (e.g., opposite the first end region) to a point proximate to the reservoir 122 such that the inlet 110 is in fluid communication with the reservoir 122. In some embodiments (not shown), the conduit 108 may enter the second end region and the inlet 110 may be disposed in the second end region (e.g., in the reservoir 122). The fluid collected in the fluid collection device 100 may be removed from the interior region of the chamber 104 via the conduit 108. The conduit 108 may include a flexible material such as plastic tubing (e.g., medical tubing) as disclosed herein. In some examples, the conduit 108 may include one or more portions that are resilient, such as having one or more of a diameter or wall thickness that allows the conduit to be flexible.

In an embodiment, one or more components of the fluid collection device 100 may include an antimicrobial material, such as an antibacterial material where the fluid collection device may contact the wearer or the bodily fluid of the wearer. The antimicrobial material may include an antimicrobial coating, such as a nitrofurazone or silver coating. The antimicrobial material may inhibit microbial growth, such as microbial growth due to pooling or stagnation of the fluids. In an embodiment, one or more components of the fluid collection device 100 (e.g., impermeable barrier 102, conduit 108, etc.) may include an odor blocking or absorbing material such as a cyclodextrine containing material or a thermoplastic elastomer (TPE) polymer.

In any of the embodiments disclosed herein, the conduits 108 may include or be operably coupled to a flow meter (not shown) to measure the flow of fluids therein, one or more securement devices (e.g., a StatLock securement device, not shown) or fittings to secure the conduit 108 to one or more components of the systems or devices disclosed herein (e.g., portable vacuum source or fluid storage container), or one or more valves to control the flow of fluids in the systems and devices herein. In an embodiment, at least one of portion of the conduit 108 of the fluid collection devices or systems herein may be formed of an at least partially opaque material which may obscure the fluids that are present therein. For example, a first section of the conduit 108 disclosed herein may be formed of an opaque material or translucent material while a second section of the conduit 108 may be formed of a transparent material or translucent material. In some embodiments, the first section may include transparent or translucent material. Unlike the opaque or nearly opaque material, the translucent material allows a user of the devices and systems herein to visually identify fluids or issues that are inhibiting the flow of fluids within the conduit 108.

In any of the examples, systems or devices disclosed herein, the system of fluid collection device may include moisture sensors (not shown) disposed inside of the chamber of the fluid collection device. In such examples, the moisture sensor may be operably coupled to a controller or directly to the portable vacuum source, and may provide electrical signals indicating that moisture is or is not detected in one or more portions of the chamber. The moisture sensor(s) may provide an indication that moisture is present, and responsive thereto, the controller or portable vacuum device may direct the initiation of suction to the chamber to remove the fluid therefrom. Suitable moisture sensors may include capacitance sensors, volumetric sensors, potential sensors, resistance sensors, frequency domain reflectometry sensors, time domain reflectometry sensors, or any other suitable moisture sensor. In practice, the moisture sensors may detect moisture in the chamber and may provide a signal to the controller or portable vacuum source to activate the portable suction device.

Figure 3A:
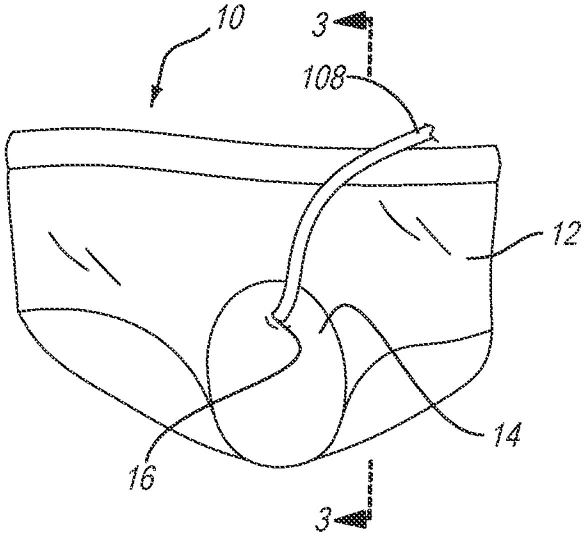
FIG. 3A is a front view of the garment for fluid collection of FIG. 1.
Figure 3B:
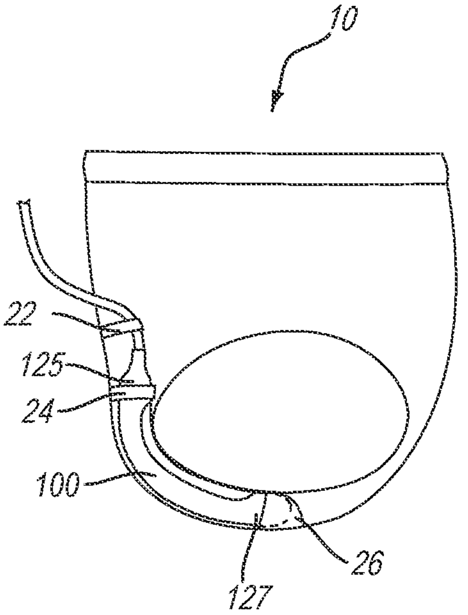
FIG. 3B is a cross-sectional side view of the garment of FIG. 3A taken along line 3-3 thereof.
Figure 3C:
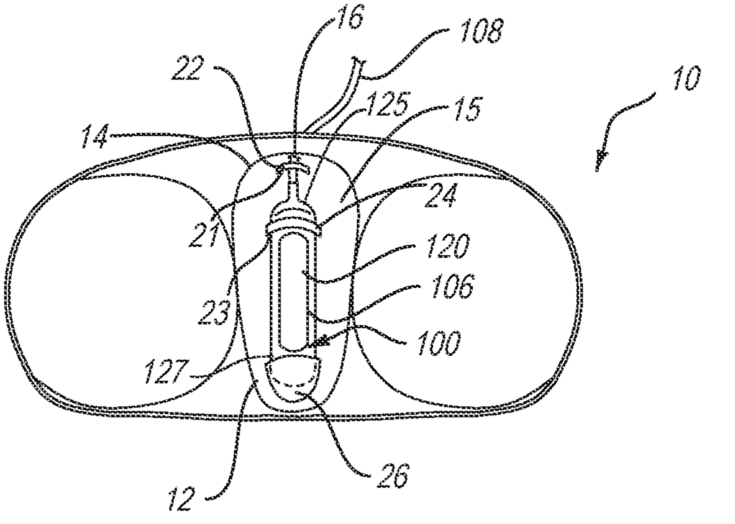
FIG. 3C is a top view of the garment of FIG. 3A.

FIGS. 3A-3C are views of the garment 10 of FIG. 1 with a fluid collection device 100, according to an embodiment. Although the fluid collection device 100 described above is shown in FIGS. 3A-3C, the garment 10 may be configured for use other fluid collection devices, including both female and male fluid collection devices. For example, according to an embodiment, a male fluid collection device may be used with the garment 10, such as the male fluid collection devices disclosed in U.S. patent application Ser. No. 16/433,773, the disclosure of which is incorporated herein by reference in its entirety.

As described above, the garment 10 may include a body, such as a fabric body 12, and a crotch portion 14. The crotch portion 14 may define or otherwise include an opening 16 (shown in FIGS. 3A and 3C) sized and dimensioned to allow the conduit 108 to pass therethrough. The opening 16 may include a diameter generally equal to the diameter of the conduit 108. In some embodiments, the opening 16 may include stretch to allow the conduit 108 to pass therethrough while fitting around the conduit 108. The opening 16, then, may result in a technical effect of allowing insertion and removal of the conduit 108 through the opening 16, as well as retention of the conduit 108 in a preferred position. In some embodiments, the opening 16 is absent (such as FIG. 4A), and the conduit may exit the garment through the waist opening or a leg opening. As shown in FIG. 3C, the crotch portion 14 may fixedly or releasably attach two portions (such as the front and back) of the fabric body 12. In some embodiments, the crotch portion 14 may be entirely surrounded by the fabric body (see, for example, FIG. 5).

With reference to FIGS. 3B and 3C, the garment 10 also includes one or more securement features on the inner surface 15 of the crotch portion 14. For example, the garment 10 includes straps 22, 24 and a pocket 26. While the garment 10 includes all three of the straps 22, 24 and the pocket 26, other embodiments may include any combination of one or more of the straps 22, 24 and the pocket 26. For example, some embodiments of the garment may include only the strap 22, only the strap 24, only the pocket 26, the strap 22 and the pocket 26, or the strap 24 and the pocket 26. Each of the securement features on the inner surface 15 of the crotch portion 14 may include a material that is the same or different from the material of the crotch portion 14. In some embodiments, one or more of the securement features may include an elastic material, silicone, polypropylene, polyethylene, polyethylene terephthalate, a polycarbonate, TPE, rubber, thermoplastic polyurethane, a woven fabric, another suitable material, or combinations thereof. The one or more straps 22, 24 and the pocket 26 result in a technical effect of allowing a user to secure the fluid collection device 100 to the garment 10 in a desired position, remove a soiled fluid collection device 100, and secure a different fluid collection device 100 to the garment 10 in the desired position.

Each of the securement features may be fixedly secured or at least partially detachably secured to the inner surface 15 of the crotch portion 14. For example, one or more of the straps 22, 24 maybe fixedly secured to the inner surface 15 of the crotch portion 14 at two portions of the straps 22, 24, such as the two ends of the straps 22, 24. With the straps 22, 24 fixedly secured to the inner surface 15 of the crotch portion 14 at two portions, through holes 21, 23 are defined or otherwise formed between the straps 22, 24 and the inner surface 15 of the crotch portion 14.

In some embodiments, one or more of the straps 22, 24 may be fixedly secured to the inner surface 15 of the crotch portion 14 at a single portion of the straps 22, 24, such as a single end of the straps 22, 24. For example, the strap 22 may be fixedly secured to the inner surface 15 of the crotch portion 14 at a first end of the strap 22, while a second end of the strap 22 distal to the first end is not fixedly secured to the inner surface 15. The strap 24 may include a similar configuration. When only a single portion or end of the straps 22, 24 is fixedly secured to the inner surface 15 of the crotch portion 14, another portion of the straps 22, 24, such as the other (or second) end of the straps 22, 24 may be configured to detachably or releasably secure to the inner surface 15 of the crotch portion 14. Straps 22, 24 having this configuration may define the through holes 21, 23 before or after the conduit 108 and or the fluid collection device 100 is positioned on the inner surface 15 of the crotch portion 14. Straps 22, 24 having this configuration also may result in the technical effect of securing varying sizes of conduits or fluid collection devices to the inner surface 15 of the crotch portion 14. In some embodiments, one or more of the straps 22, 24 may not be fixedly secured (e.g., fixed securement is absent from one or more of the straps 22, 24), and two portions or ends of the straps 22, 24 are configured to detachably or releaseably secure to the inner surface 15 of the crotch portion 14.

Similar to the straps 22, 24, the pocket 26 maybe fixedly secured to the inner surface 15 of the crotch portion 14 at two portions of the pocket 26, such as two edges of the pocket 26. With the pocket 26 fixedly secured to the inner surface 15 of the crotch portion 14 at two portions, an opening and a cavity is defined or otherwise formed between the pocket 26 and the inner surface 15 of the crotch portion 14. The two edges of the pocket 26 fixedly secured to the inner surface 15 may connect at a distal end of the pocket 26 distal to the opening of the pocket 26. Alternatively, a gap may be positioned between the two edges of the pocket 26 fixedly secured to the inner surface 15.

In some embodiments, the pocket 26 may be fixedly secured to the inner surface 15 of the crotch portion 14 at a single portion of the pocket 26, such as a single edge of the pocket 26. For example, the pocket 26 be fixedly secured to the inner surface 15 of the crotch portion 14 at a first edge of the pocket 26, while a second edge of the pocket distal to the first edge is not fixedly secured to the inner surface 15. When only a single portion or edge of the pocket 26 is fixedly secured to the inner surface 15 of the crotch portion 14, another portion of the pocket 26, such as the other (or second) edge of the pocket may result in the technical effect of detachably or releasably securing the pocket 26 to the inner surface 15 of the crotch portion 14. A pocket 26 having this configuration may define the cavity before or after the fluid collection device 100 is positioned on the inner surface 15 of the crotch portion 14. A pocket 26 having this configuration also may result in the technical effect of securing varying sizes of fluid collection devices to the inner surface 15 of the crotch portion 14. In some embodiments, the pocket 26 may not be fixedly secured (e.g., fixed securement is absent from the pocket), and two portions or edges of the pocket 26 are configured to detachably or releaseably secure to the inner surface 15 of the crotch portion 14.

Securement features that are fixedly secured to the inner surface 15 of the crotch portion 14 may be fixedly secured to the inner surface 15 with one or more of an adhesive, a threaded seam, ultrasonic welding, other suitable securements, or combinations thereof. Securement features that are configured to detachably or releaseably secure to the inner surface 15 of the crotch portion 14 may include one or more of hook and loop fasteners, buttons, snaps, clips, magnets, or any other fastener, with the inner surface 15 of the crotch portion 14 having a corresponding fastener.

The securement features are positioned or are positionable on the inner surface 15 of the crotch portion 14 to provide the technical effect of positioning the opening 106 and the fluid permeable body 120 of the fluid collection device 100 proximate or adjacent to a urethra of the user 5 (e.g., over, on, or covering the urethra of the user 5). Though the user 5 is not shown, FIG. 3B shows how the fluid collection device 100 may bend to conform to the shape in the pelvic region of the user 5 to position the opening 106 and the fluid permeable body 120 of the fluid collection device 100 proximate or adjacent to a urethra of the user 5 when the fluid collection device is secured to inner surface 15 of the crotch portion 14.

In an embodiment, the strap 22 is positioned or positionable on the inner surface 15 of the crotch portion 14 to secure a portion of the conduit 108 to the inner surface 15. The strap 22 at least partially defines the through hole 21 between the strap 22 and the inner surface 14. The conduit 108 includes a portion disposed outside the chamber 104 of the fluid impermeable barrier 102, and the through hole 21 may be sized and dimensioned to hold a segment of that portion of the conduit within the through hole 21.

In an embodiment, the strap 24 is positioned or positionable on the inner surface 15 of the crotch portion 14 to secure the first end region 125 to the inner surface 15. The strap 24 at least partially defines the through hole 23 between the strap 24 and the inner surface 14. The through hole 23 may be sized and dimensioned to hold a portion of the first end region 125 of the fluid impermeable barrier 102 within the through hole 22. The elasticity or flexibility of the strap 24 may result in the strap 24 having the technical effect of stretching around a portion of the first end region 125 to secure the first end region 125 within the through hole 23.

In an embodiment, the pocket 26 is positioned or positionable on the inner surface 15 of the crotch portion 14 to secure at least a portion of the second end region 127 within the pocket 26. The pocket 26 at least partially defines a cavity of the pocket 26. The pocket 26 and the cavity may be sized and dimensioned to hold at least a portion of the second end region 127 of the fluid impermeable barrier 102 within the cavity of the pocket 26. The pocket 26 may extend at least partially from an end of the fluid impermeable barrier 102 to the opening 106 when the second end region 127 is at least partially positioned within the pocket 26. The elasticity or flexibility of the pocket 26 may result in the technical effect of the pocket 26 stretching around a portion of the second end region 127 to secure the second end region 127 within the through cavity of the pocket 26.

While FIGS. 3A-3C show the fluid collection device 100 secured to the garment 10, other fluid collection devices may be secured to the inner surface 15 of the crotch portion 14. For example, straps 22, 24 may secured around the conduit and a portion of a male fluid collection device. Moreover, the garments herein may have different forms including: pants; shorts; undergarments such as briefs, boxer briefs, a thong, a jock strap, etc.; a sanitary belt; or the like.

Figure 4A:
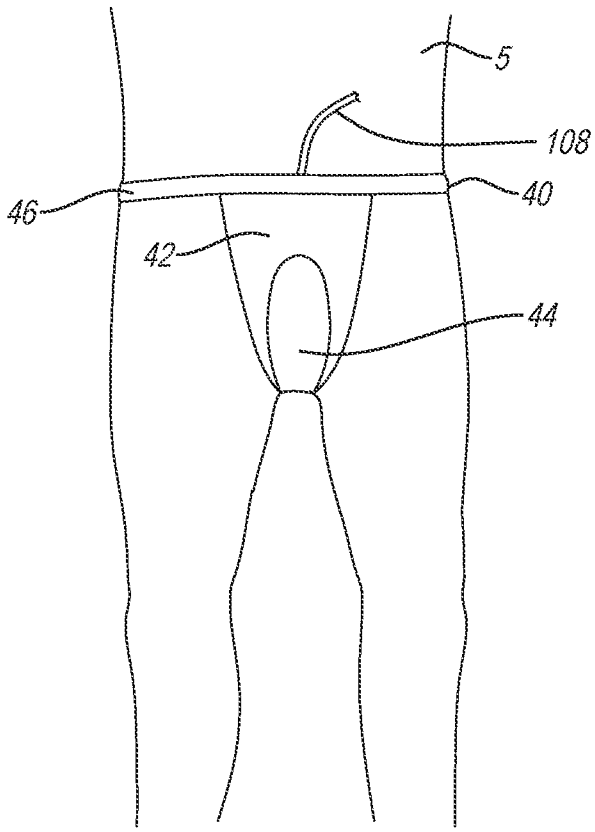
FIG. 4A is a front view of a garment for fluid collection worn on a user, according to an embodiment.
Figure 4B:
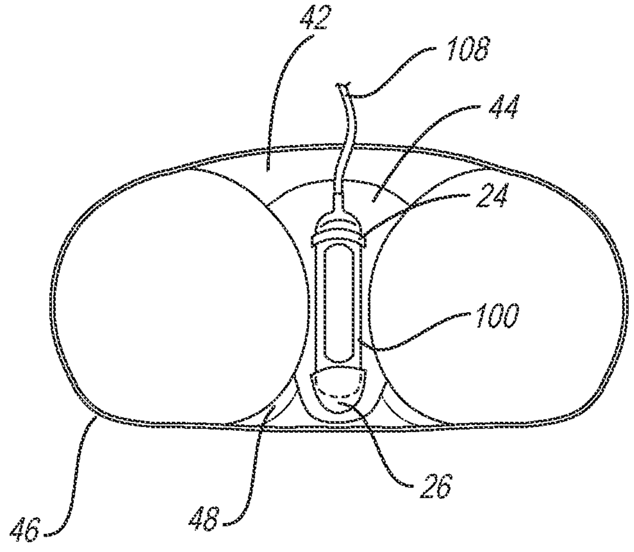
FIGS. 4B and 4C are views of the garment of FIG. 4A with a fluid collection device, according to an embodiment.
Figure 4C:
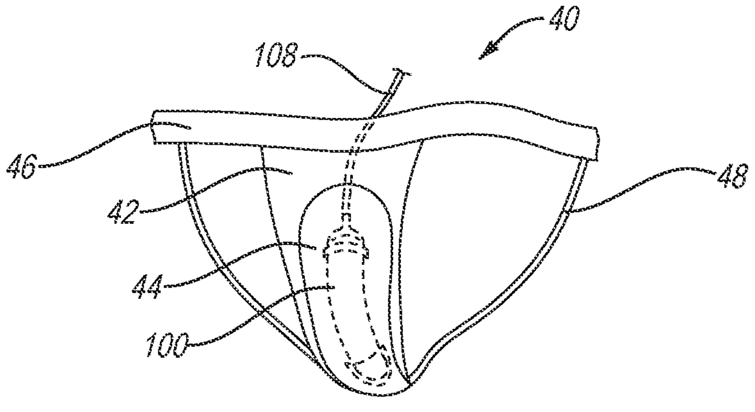

Turning now to FIGS. 4A-C, which provide views of a garment 40 for fluid collection, according to an embodiment. The garment 40 may be similar or identical to the garment 10 in one or more aspects, but sized, shaped, and otherwise configured as a jock strap. Unless otherwise noted, the garment 40 may include any of the technical effects described in relation to the garment 10. The garment 40 includes a fabric body 42 that is sized and shaped to fit on a portion of a pelvis of the user 5 and maintain position thereon, as shown in FIG. 4A. The fabric body 42 of the garment 40 may be similar or identical to the fabric body 12 in one or more aspects. The fabric body 42 of the garment 40 includes a crotch portion 44 therein. The crotch portion 44 of the garment 40 may be similar or identical to the crotch portion 14 in one or more aspects. For example, the crotch portion 44 may be positioned in the crotch of the garment 40. The crotch portion 44 is positioned over the region of the urethra of the wearer (e.g., within the region of the crotch) when the garment 40 is worn. The crotch portion 44 includes one or more of the securement features described above in relation to the crotch portion 14. For example, FIGS. 4B and 4C show the crotch portion 44 includes the strap 24 and the pocket 26, and the strap 22 is absent. In other embodiments, the crotch portion 44 may include both of the straps 22, 24 and also the pocket 26. In some embodiments, the crotch portion 44 may include the strap 22 and the pocket 26, and the strap 24 may be absent. The securement features of the crotch portion 44 may include any aspects and technical effects of the securement features of the crotch portion 14, such as fixed securement and/or detachable securement to the inner surface of the crotch portion 44. A fluid collection device (e.g., 100) may be secured to the crotch portion 44, such that fluids in the region (e.g., urine) may be collected by the fluid collection device. The conduit opening may be absent from the crotch portion 44, and the conduit 108 may exit the garment 40 through the opening at the waistband 46 (shown in FIGS. 4A and 4C) or one of the leg openings. When secured to the crotch portion 44, the fluid collection device 100 may take shape around the pelvic region of the user 5, as described above in relation to the garment 10. Accordingly, the garment 40 and securement features of the crotch portion 44 may serve to align the fluid collection device 100 with the urethra of the user such that fluids originating therefrom can be collected before soiling clothing or bedding.

The garment 40 also includes a waistband 46 and two straps 48 extending from the crotch portion 44 to the waistband 48. The straps 48 extend over the buttocks of the user 5, and may be secured directly to crotch portion 44 or may be secured to the fabric body 42. The fabric body 42 may be positioned only at the front of the garment 40 such that the fabric body 42 extends only between the waistband 46 and the crotch portion 44 in the front, and the straps 48 extend between the crotch portion 44 and the waistband 46 in the rear of the garment 40 in the absence of the fabric body 42. In some examples, the fabric body 42 surrounds the crotch portion 44, and the straps 48 may be secured to the fabric body 42.

Figure 5:
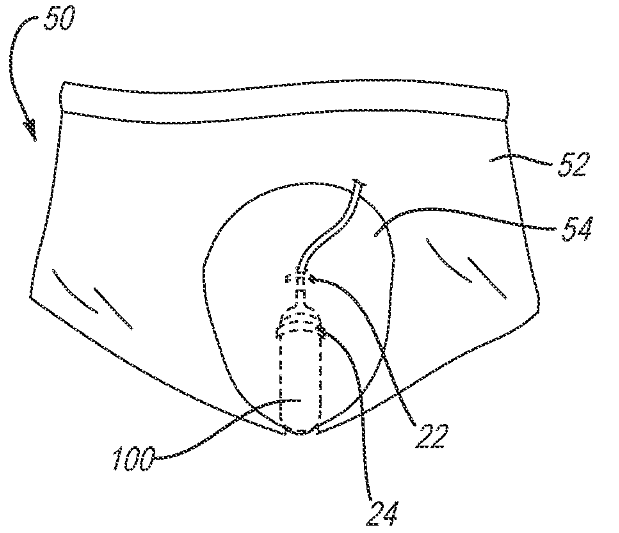
FIGS. 5-7 are front views of garments for fluid collection, according to various embodiments.

FIG. 5 is a front view of a garment 50 for fluid collection, according to an embodiment. The garment 50 may be similar or identical to the garment 10 in one or more aspects and, unless otherwise noted, may include any of the technical effects described above in relation to the garment 10. The garment 50 includes a fabric body 52 that is sized and shaped to fit on a pelvis of a wearer and maintain position thereon. The fabric body 52 may be sized, shaped, and configured to form undergarments in the form of boxer briefs or shorts. The fabric body 52 of the garment 50 may be similar or identical to the fabric body 12 in one or more aspects. The garment 50 also includes a crotch portion 54. The crotch portion 54 of the garment 50 may be similar or identical to the crotch portion 14 or the crotch portion 44 in one or more aspects. For example, the crotch portion 54 is positioned over the region of the urethra of the wearer (e.g., within the region of the crotch) when the garment 50 is worn. A fluid collection device (e.g., 100) may be secured to the crotch portion 54 with one or more securement features, such that fluids in the region (e.g., urine) may be collected by the fluid collection device. Accordingly, the garment 50 and crotch portion 54 may serve to align the fluid collection device 100 with the urethra of the user such that fluids originating therefrom can be collected before soiling clothing or bedding.

Figure 6:
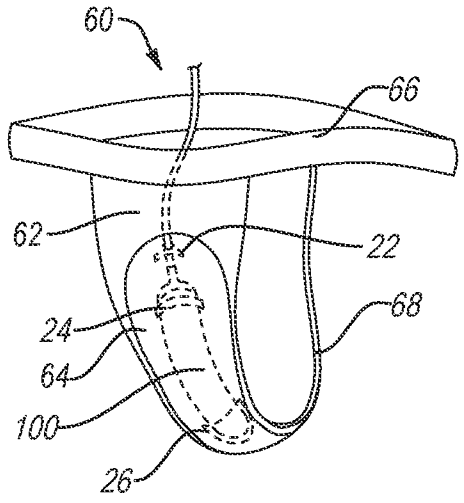

FIG. 6 is a front view of a garment 60 for fluid collection, according to an embodiment. The garment 60 may be similar or identical to the garment 10, 40, or 50 in one or more aspects and, unless otherwise noted, may include of the technical effects described above in relation to the garment 10. The garment 60 includes a fabric body 62 that is sized and shaped to fit on a pelvis of a wearer and maintain position thereon. The fabric body 62 may be sized, shaped, and configured to form undergarments in the form of thong underwear having a waistband 66 and a back strap 68 that fits between the buttocks of the user 5. The fabric body 62 of the garment 60 may be similar or identical to the fabric body 12 in one or more aspects. The garment 60 includes a crotch portion 64. The crotch portion 64 of the garment 60 may be similar or identical to the crotch portion 14, 44, or 54 in one or more aspects. The crotch portion 64 is positioned over the region of the urethra of the wearer (e.g., within the region of the crotch) when the garment 60 is worn. A fluid collection device (e.g., 100) may be secured to the crotch portion 64 with one or more securement features, such that fluids in the region (e.g., urine) may be collected by the fluid collection device. Accordingly, the garment 60 and crotch portion 64 may serve to align the fluid collection device with the urethra of the user such that fluids originating therefrom can be collected before soiling clothing or bedding.

Figure 7:
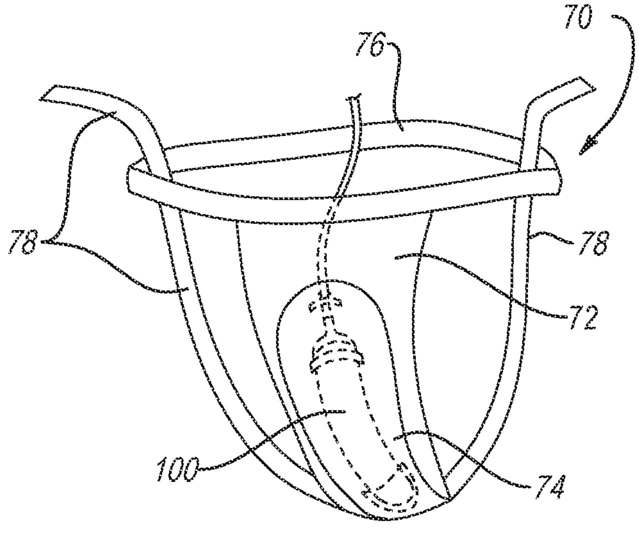

FIG. 7 is a front view of a garment 70 for fluid collection, according to an embodiment. The garment 70 may be similar or identical to the garment 10, 40, 50, or 60 in one or more aspects and, unless otherwise noted, may include any of the technical effects described above in relation to the garment 10. The garment 70 includes a fabric body 72 that is sized and shaped to fit on a pelvis of a wearer and maintain position thereon. The fabric body 72 may be sized, shaped, and configured to form undergarments in the form of a jock strap. The fabric body 72 of the garment 70 may be similar or identical to the fabric body 12 in one or more aspects. The garment 70 includes a crotch portion 74. The crotch portion 74 of the garment 70 may be similar or identical to the crotch portion 14, 44, 54, or 64 in one or more aspects. The crotch portion 74 is positioned over the region of the urethra of the wearer (e.g., within the region of the crotch) when the garment 70 is worn. A fluid collection device (e.g., 100) may be secured to the inner surface of the crotch portion 74 with one or more securement features, such that fluids in the region (e.g., urine) may be collected by the fluid collection device. Accordingly, the garment 70 and crotch portion 74 thereon may serve to align the fluid collection device with the urethra of the user such that fluids originating therefrom can be collected before soiling clothing or bedding.

In some examples, the garment may be adjustable to provide the technical effect of adjusting the position of the crotch portion 74 with respect to the urethral region of the wearer. For example, the garment may include one or more adjustable straps 78. The one or more adjustable straps 78 may attach to crotch portion 74 and the waistband 76. The waistband 76 and the one or more adjustable straps 78 may have complementary connections (e.g., button and button holes, hook and loop strips, etc.). The adjustable straps 78 may include multiple connection features (e.g., multiple buttons, hook and loop strips, etc.) along the body of the strap to allow adjustment of the length of the adjustable straps between the waistband 76 and the crotch portion 74. In some examples, the waistband 76 may be expandable or contractible. The adjustable straps 78 may provide the technical effect of selectively changing the location of the fluid collection device with respect to the urethral region of the wearer. Accordingly, the garment 70, adjustable straps 76, and crotch portion 74 may result in the technical effect of aligning the fluid collection device with the urethra of the user such that fluids originating therefrom can be collected before soiling clothing or bedding.

Any of the garments disclosed herein may be adjustable in one or more dimensions to selectively adjust the position of the crotch portion and fluid collection device therein with respect to a urethral region of the wearer. Accordingly, a single garment may be used for a wide variety of sizes of users.

Figure 8:
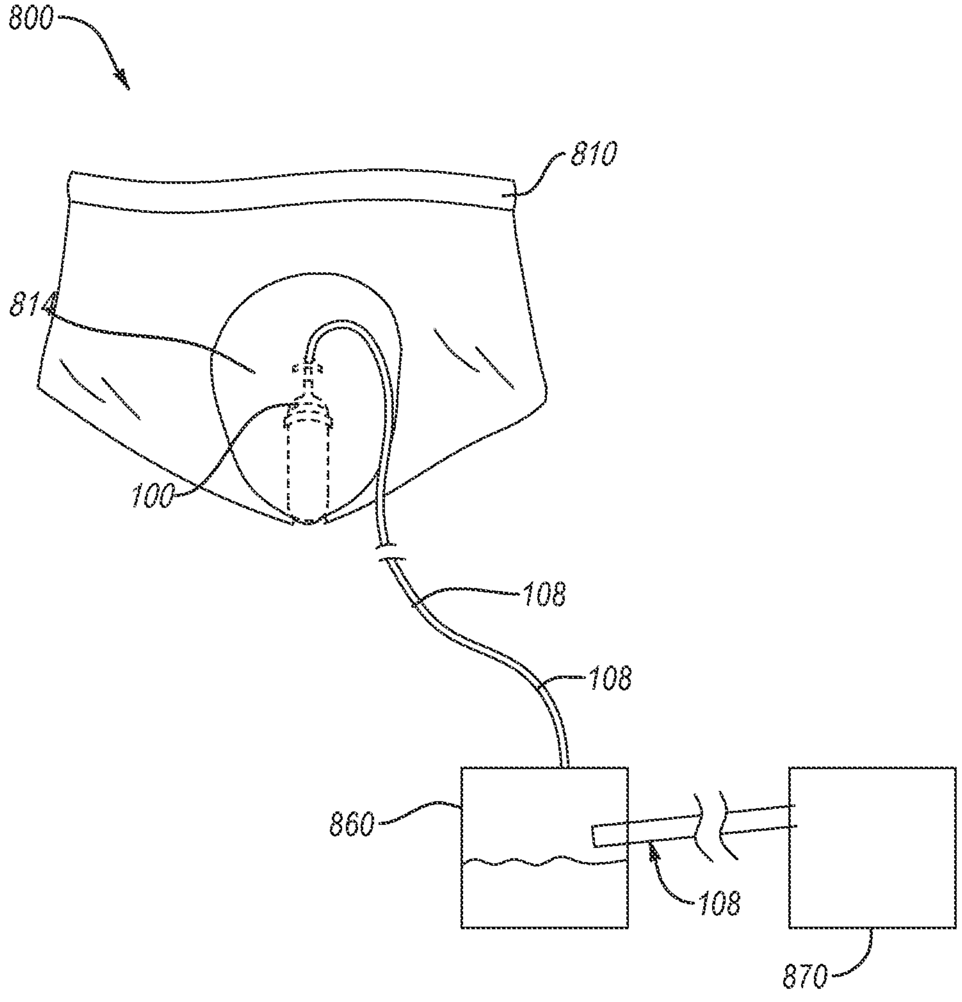
FIG. 8 is a block diagram of a system for fluid collection, according to an embodiment.

FIG. 8 is a block diagram of a system 800 for fluid collection, according to an embodiment. The system 800 includes a garment 810 having a fluid collection device 100 secured thereto on a crotch portion 814, a fluid storage container 860, and a vacuum source 870. The fluid collection device 100, the fluid storage container 860, and the vacuum source 870 may be in fluid communication with each other via one or more conduits 108. For example, fluid collection device 100 may be operably coupled to (e.g., in fluid communication with) one or more of the fluid storage container 860 or the portable source 870 via the conduits 108. The garment 810 may be similar or identical to any of the garments disclosed herein, such as garment 10, 40, 50, 60, or 70. The fluid collection device 100 may be similar or identical to any of the fluid collection devices disclosed herein, such as a male or female fluid collection device.

Fluid (e.g., urine or other bodily fluids) collected in the fluid collection device 100 may be removed from the fluid collection device 100 via the conduit 108 which protrudes into an interior region of the fluid collection device 801. For example, a first open end of the conduit 108 may extend into the fluid collection device 100 to a reservoir therein. The second open end of the conduit 108 may extend into the fluid collection device 100 or the vacuum source 870. The suction force may be introduced into the interior region of the fluid collection device 100 via the first open end of the conduit 108 responsive to a suction (e.g., vacuum) force applied at the second end of the conduit 108. The suction force may be applied to the second open end of the conduit 108 by the vacuum source 870 either directly or indirectly.

The suction force may be applied indirectly via the fluid storage container 860. For example, the second open end of the conduit 108 may be disposed within the fluid storage container 860 and an additional conduit 108 may extend from the fluid storage container 860 to the vacuum source 870. Accordingly, the vacuum source 870 may apply suction to the fluid collection device 100 via the fluid storage container 860. In some examples, the suction force may be applied directly via the vacuum source 870. For example, the first open end of the conduit 108 may be disposed in the fluid collection device 100 and the second open end of the conduit 108 may be disposed within the vacuum source 870. An additional conduit 108 may extend from the vacuum source 870 to a point outside of the fluid collection device 100, such as to the fluid storage container 860. In such examples, the vacuum source 870 may be disposed between the fluid collection device 100 and the fluid storage container 860.

In examples, the fluid storage container 860 may include a bag (e.g., drainage bag), a bottle or cup (e.g., collection jar), tubing, or any other container for storing bodily fluids such as urine. In examples, the conduit 108 may extend from the fluid collection device 100 and attach to the fluid storage container 860 at a first point therein. An additional conduit 108 may attach to the fluid storage container 860 at a second point thereon and may extend and attach to the vacuum source 870. For example, the fluid storage container 860 may include a container in fluid communication with a first conduit section that is also in fluid communication with the fluid collection device 100. The container may be in fluid communication with a second section of the conduit 108 that is also in fluid communication with the vacuum source. In such examples, the vacuum source 870 may provide a vacuum/suction through the container to the fluid collection device 100 to provide suction in the chamber of the fluid collection device. Accordingly, a vacuum (e.g., suction) may be drawn through fluid collection device 801 via the fluid storage container 860. As the fluid is drained from the chamber, the fluid may travel through the first section of conduit to the fluid storage container where it may be retained. Fluid, such as urine, may be drained from the fluid collection device 100 using the vacuum source 870.

The vacuum source 870 may include one or more of a manual vacuum pump, and electric vacuum pump, a diaphragm pump, a centrifugal pump, a displacement pump, a magnetically driven pump, a peristaltic pump, or any pump configured to produce a vacuum. The vacuum source 870 may provide a vacuum or suction to remove fluid from the fluid collection device 100. In examples, the vacuum source 870 may be powered by one or more of a power cord (e.g., connected to a power socket), one or more batteries, or even manual power (e.g., a hand operated vacuum pump). The vacuum sources 870 disclosed herein may include one or more of a switch, a button, a plug, a remote, or any other device suitable to activate the vacuum source 870.

Figure 9:
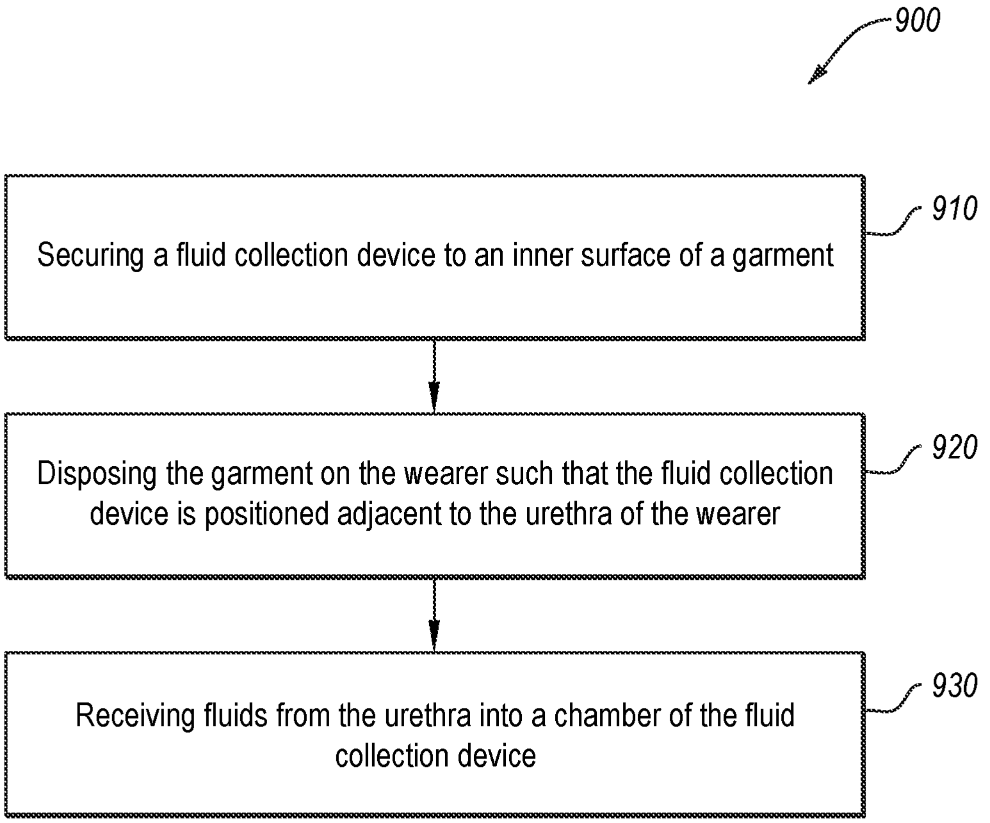
FIG. 9 is a flow diagram of a method to collect fluid, according to an embodiment.

FIG. 9 is a flow diagram of a method 900 to collect fluid, according to an embodiment. The method 900 can include act 910, which recites "securing a fluid collection device to an inner surface of a garment." Act 910 may be followed by act 920, which recites "disposing the garment on the wearer such that the fluid collection device is positioned adjacent to the urethra of the wearer." Act 920 may be followed by act 930, which recites "receiving fluids from the urethra into a chamber of the fluid collection device."

Acts 910, 920, 930 of the method 900 are for illustrative purposes. For example, the act 910, 920, 930 of the method 900 can be performed in different orders, split into multiple acts, modified, supplemented, or combined. In an example, one or more of the acts 910, 920, 930 of the method 900 can be omitted from the method 900. For example, the method 900 may not include the act 910. Any of the acts 910, 920, or 930 can include using any of the garments, fluid collection devices, vacuum sources, fluid storage containers, systems, or components of the same disclosed herein. For example, the garment may include a crotch portion having an inner surface with one or more securement features secured thereto. The fluid collection device may include a fluid impermeable barrier at least partially defining the chamber, the fluid impermeable barrier also defining an opening extending therethrough, the opening configured to be positioned adjacent to a female urethra or have a male urethra positioned therethrough. The fluid collection device may include a wicking material disposed with the chamber and a conduit disposed within wicking material, the conduit including an inlet positioned within the fluid collection device and an outlet.

Act 910 recites "securing a fluid collection device to an inner surface of a garment." In some examples, act 910 includes at least one of (1) securing a first end region of a fluid impermeable barrier of the fluid collection device in a through hole defined by a portion of the inner surface of a crotch portion and a strap secured to the inner surface, (2) inserting a second end region of the fluid impermeable barrier of the fluid collection device in a pocket on the inner surface of the pocket, or (3) inserting a conduit to an additional through hole defined by a portion of the inner surface and an additional strap secured to the inner surface. Act 910 may include multiple acts, such as any combination of securing the first end region with the strap, inserting the second region in the pocket, and/or inserting the conduit in the through hole formed with the additional strap.

In some embodiments, one or more of the straps on the inner surface of the crotch portion may be at least partially detachably securable to the inner surface of the crotch portion. The act of securing a first end region of a fluid impermeable barrier of the fluid collection device in a through hole defined by a portion of the inner surface of a crotch portion and a strap secured to the inner surface, then, may include positioning the strap over the first end region of the fluid impermeable device with the fluid impermeable device between the strap and the inner surface, and then securing an end of the strap to the inner surface.

The fluid collection device may be a female fluid collection device and the garment may include a crotch portion configured to secure the female fluid collection device therein. The fluid collection device may be a male fluid collection device and the garment may include a crotch portion configured to secure the male fluid collection device therein. The crotch portion may be positioned on the garment according to the sex of the intended wearer.

Act 920 recites, "disposing the garment on the wearer such that the fluid collection device is positioned adjacent to the urethra of the wearer." Disposing the garment on the wearer such that the fluid collection device is positioned adjacent to the urethra of the wearer can include donning the garment or placing the garment on the wearer prior to, after, or contemporaneously with positioning a fluid collection device on the inner surface of the crotch portion of a garment. Disposing the garment on the wearer such that the fluid collection device is positioned adjacent to the urethra of the wearer may include disposing the garment on the wearer such that the fluid collection device is positioned adjacent to the urethra of the wearer when the fluid collection device is positioned therein. For example, disposing the garment on the wearer such that the fluid collection device is positioned adjacent to the urethra of the wearer may be performed prior to act 910. Disposing the garment on the wearer such that the fluid collection device is positioned adjacent to the urethra of the wearer can include donning or placing any of the garments disclosed herein on the wearer. For example, disposing the garment on the wearer such that the fluid collection device is positioned adjacent to the urethra of the wearer may include adjusting one or more dimensions of the garment with adjustable straps thereon to place the crotch portion or the fluid collection device secured thereto over the urethra of the wearer.

In some examples, disposing the garment on the wearer such that the fluid collection device is positioned adjacent to the urethra of the wearer can include positioning the opening of a female fluid collection device such that the fluid permeable membrane of the female fluid collection device abuts or is positioned proximate to the female urethra. For example, positioning an opening of a fluid collection device adjacent to a female urethra of a user may include positioning opening of the fluid collection device, secured to the inner surface of the crotch portion of the garment, on or between the labia of a wearer.

Act 930 recites "receiving fluids from the urethra into a chamber of the fluid collection device." For example, act 930 can include wicking the fluids away from urethra via the opening using wicking material (e.g., fluid permeable membrane and a fluid permeable support). In some examples, act 930 can include receiving the fluids into the chamber of the fluid collection device. In either example, act 930 can include flowing the fluid towards a portion of the chamber that is in fluid communication with an inlet of a conduit in fluid communication a vacuum source. For instance, act 930 can include flowing the fluids to a substantially unoccupied portion of the chamber (e.g., a reservoir), to a gravimetrically low point of the chamber, etc.

The method 900 may include applying suction with a vacuum source effective to suction the fluids from the chamber via a conduit disposed therein that is in fluid communication with the vacuum source. In examples, applying suction with a vacuum source effective to suction the fluids from the chamber via a conduit disposed therein that is in fluid communication with the vacuum source can include using any of the vacuum sources disclosed herein. In an example, applying suction can include activating the vacuum source (e.g., suction device) in fluid communication with the inlet of the conduit in the fluid collection device. In examples, activating the vacuum source in fluid communication with the inlet of the conduit in the fluid collection device can include supplying power to the vacuum source by one or more of flipping an on/off switch, pressing a button, plugging the vacuum source into a power outlet, putting batteries into the vacuum source, etc. In examples, the vacuum source may include a hand operated vacuum pump and applying suction with a vacuum source may include manually operating the hand operated vacuum pump effective to suction the fluids from the chamber via the conduit disposed therein that is in fluid communication with the vacuum source.

In examples, applying suction with a vacuum source effective to suction the fluids from the chamber via a conduit disposed therein that is in fluid communication with the vacuum source can be effective to remove at least some fluid (e.g., urine) from the chamber (e.g., interior region) of the fluid collection device. In examples, applying suction with a vacuum source effective to suction the fluids from the chamber via a conduit disposed therein that is in fluid communication with the vacuum source can be effective to transfer at least some of the fluid from the chamber of the fluid collection device to a fluid storage container (e.g., a bottle or bag) in fluid communication with the vacuum source and the fluid collection device. In examples, the vacuum source may be spaced from the fluid collection device.

In examples, applying suction with a vacuum source effective to suction the fluids from the chamber via a conduit disposed therein that is in fluid communication with the vacuum source may include detecting moisture in the chamber (e.g., via one or more moisture sensors) and responsive thereto, activating the vacuum source to provide suction in the chamber. Control of the vacuum source responsive to the signals indicating that moisture or a threshold level thereof is present in the chamber can be automatic, such as via a controller, or may merely provide an indication that a level of moisture is present that may necessitate removal of fluid from the chamber of the fluid collection device. In the latter case, a user may receive the indication and activate the vacuum pump.

In an example, the method 900 can include collecting the fluids that are removed from the fluid collection device, such as into a fluid storage container that is spaced from the fluid collection device that is in fluid communication with the conduit. The fluid storage container can include any of the fluid storage containers disclosed herein.

In an example, the fluid collection device (such as a soiled fluid collection device) may be removed from the garment and replaced with a replacement fluid collection device. Accordingly, the method 900 can include an act of removing the fluid collection device from the garment and an act of securing a replacement fluid collection device to the inner surface of the garment. Securing the replacement fluid collection device to the inner surface of the garment may include at least one of (1) securing a first end region of a fluid impermeable barrier of the replacement fluid collection device in the through hole defined by the portion of the inner surface of the crotch portion and the strap secured to the inner surface, (2) inserting a second end region of the fluid impermeable barrier of the replacement fluid collection device in the pocket on the inner surface of the pocket, or (3) inserting a conduit to the additional through hole defined by the portion of the inner surface and the additional strap secured to the inner surface.

Devices and methods described herein can be configured to collect urine from a male user, such as having a fluid collection device shaped and sized to receive a male urethra (e.g., penis) therein. In examples, the method 900 can include positioning a receptacle of a male fluid collection device around the male urethra such that the male urethra is positioned in the receptacle.

As used herein, the term "about" or "substantially" refers to an allowable variance of the term modified by "about" by ±10% or ±5%. Further, the terms "less than," "or less," "greater than", "more than," or "or more" include as an endpoint, the value that is modified by the terms "less than," "or less," "greater than," "more than," or "or more."

While various aspects and embodiments have been disclosed herein, other aspects and embodiments are contemplated. The various aspects and embodiment disclosed herein are for purposes of illustration and are not intended to be limiting.

What is claimed is:

1. A fluid collection system, comprising:

a garment configured to be worn on a pelvis of a user, the garment including at least a crotch portion having an inner surface, a first securement feature including a first strap at least partially defining a through hole between the first strap and the inner surface and a second securement feature spaced from the first securement feature and including at least one of (1) a second strap partially defining a through hole between the second strap and the inner surface or (2) a pocket on the inner surface of the crotch portion; and a fluid collection device having at least a portion sized and shaped to fit within one or more of the at least one of the through hole of the first strap, the through hole of the second strap, or the pocket, the fluid collection device including:

a fluid impermeable barrier at least partially defining a chamber, an opening extending longitudinally along the fluid impermeable barrier and configured to be positioned adjacent to a urethra of the user, and an aperture configured to receive a conduit therethrough; and a fluid permeable body positioned at least partially within the chamber to extend across at least a portion of the opening and configured to wick fluid away from the opening, wherein the first securement feature and the second securement feature are positioned on the crotch portion of the garment and the fluid collection device is sized to position the opening and the fluid permeable body at least proximate to the urethra of the user.

2. The fluid collection system of claim 1, wherein the fluid collection device includes a generally cylindrical shape and wherein the through hole of the first strap is sized and dimensioned to hold the fluid impermeable barrier within the through hole.

3. The fluid collection system of claim 2, wherein the fluid impermeable barrier includes a first end region between the opening and the aperture, and the first strap is positioned on the crotch portion of the garment to hold the first end region of the fluid impermeable barrier within the through hole.

4. The fluid collection system of claim 2, wherein at least one end of the first strap is releasably secured to the inner surface.

5. The fluid collection system of claim 2, wherein the fluid impermeable barrier includes a second end region distal to the aperture and the second securement feature of the garment includes at least the pocket on the inner surface of crotch portion, the pocket being sized and dimensioned to hold the second end region within the pocket such that the opening in the fluid impermeable barrier is disposed between the pocket and the first strap.

6. The fluid collection system of claim 1, wherein the crotch portion includes a wicking material.

7. The fluid collection system of claim 1, further comprising:

a conduit extending through the aperture such that a first portion of the conduit is disposed within the chamber and a second portion of the conduit is disposed outside the chamber; and wherein the second securement feature includes at least the second strap secured to the inner surface of the garment and at least partially defining the through hole of the second strap between the additional strap and the inner surface, wherein the through hole of the second strap is sized and dimensioned to hold a segment of the second portion of the conduit within the through hole of the second strap.

8. The fluid collection system of claim 1, wherein the crotch portion includes an opening sized to receive the conduit therethrough.

9. The fluid collection system of claim 1, wherein the garment includes one or more adjustable straps configured to alter a position of the crotch portion and the fluid collection device with respect to the urethra of the user.

10. A fluid collection system, comprising:

a garment configured to be worn on a pelvis of a user, the garment including at least a crotch portion having an inner surface and a strap secured to the inner surface of the garment and at least partially defining a through hole between the strap and the inner surface;

a fluid collection device including:

a fluid impermeable barrier at least partially defining a chamber, an opening extending longitudinally along the fluid impermeable barrier and configured to be positioned adjacent to a urethra of the user, and an aperture configured to receive a conduit therethrough; and a fluid permeable body positioned at least partially within the chamber to extend across at least a portion of the opening and configured to wick fluid away from the opening; and a conduit extending through the aperture such that a first portion of the conduit is disposed within the chamber and a second portion of the conduit is disposed outside the chamber, the conduit having at least a portion sized and shaped to fit within the through hole, wherein the strap is positioned on the crotch portion of the garment to receive the second portion of the conduit therethrough and the fluid collection device is sized to position the opening and the fluid permeable body at least proximate to the urethra of the user.

11. The fluid collection system of claim 10, wherein at least one end of the strap is releasably secured to the inner surface.

12. The fluid collection system of claim 10, wherein the fluid impermeable barrier includes a second end region distal to the aperture and the garment includes a pocket on the inner surface of crotch portion spaced from the strap and sized and dimensioned to hold the second end region of the fluid impermeable barrier within the pocket.

13. The fluid collection system of claim 12, wherein the crotch portion includes a wicking material.

14. The fluid collection system of claim 10, wherein the garment includes a fluid absorption material.

15. The fluid collection system of claim 10, wherein the crotch portion includes an opening sized to receive the conduit therethrough.

16. The fluid collection system of claim 10, wherein the garment includes one or more adjustable straps configured to alter a position of the crotch portion and the fluid collection device with respect to the urethra of the user.

17. A method of collecting fluid, the method comprising:

securing a fluid collection device to an inner surface of a garment by at least one of:

securing a first end region of a fluid impermeable barrier of the fluid collection device in a through hole defined by a portion of the inner surface and a strap secured to the inner surface; and inserting a second end region of the fluid impermeable barrier of the fluid collection device in a pocket on the inner surface of the garment, the pocket being spaced from the strap such that an opening in the fluid impermeable barrier is disposed between the pocket and the strap;

disposing the garment on the wearer such that the opening in the fluid impermeable barrier and a fluid permeable body disposed in a chamber defined by the fluid impermeable barrier are positioned adjacent to the urethra of the wearer; and receiving fluids from the urethra into the chamber.

18. The method of claim 17, wherein securing the fluid collection device to the inner surface of the garment includes both:

securing the first end region of the fluid impermeable barrier in the through hole defined by the portion of the inner surface and the strap secured to the inner surface; and inserting the second end region of the fluid impermeable barrier of the fluid collection device on the inner surface of the pocket.

19. The method of claim 17, wherein securing the first end region of the fluid impermeable barrier in the through hole defined by the portion of the inner surface and the strap secured to the inner surface includes:

positioning the strap over the first end region of the fluid impermeable device with the fluid impermeable device between the strap and the inner surface; and securing an end of the strap to the inner surface.

20. The method of claim 17, wherein securing the fluid collection device to the inner surface of the garment includes inserting a conduit to an additional through hole defined by a portion of the inner surface and an additional strap secured to the inner surface.

21. The method of claim 17, wherein disposing the garment on the wearer is performed after securing the fluid collection device to the inner surface of the garment.

22. The method of claim 17, further comprising:

removing the fluid collection device from the garment; and securing a replacement fluid collection device to the inner surface of the garment by at least one of:

securing a first end region of a fluid impermeable barrier of the replacement fluid collection device in the through hole defined by the portion of the inner surface and the strap secured to the inner surface; or inserting a second end region of the fluid impermeable barrier of the replacement fluid collection device in the pocket on the inner surface of the pocket.

23. A garment configured to be worn on a pelvis of a user to collect fluid, the garment comprising:

a waistband; and at least a crotch portion having:

an inner surface;

a strap partially defining a through hole between the strap and the inner surface, the through hole being sized and dimensioned to secure a conduit or a first end region of a fluid impermeable barrier of a fluid collection device therein; and a pocket on the inner surface of the crotch portion, the pocket being sized and dimensioned to secure the second end region of a fluid impermeable barrier of the fluid collection device therein, wherein the strap and the pocket are positioned on the inner surface of the crotch portion to position an opening and a fluid permeable body of the fluid collection device at least proximate to a urethra of the user and between the strap and the pocket when the fluid collection device is secured to the inner surface with the strap and the pocket.

24. The garment of claim 23, wherein the through hole is sized and dimensioned to hold the first end region the fluid impermeable barrier within the through hole.

25. The garment of claim 24, wherein at least one end of the strap is releasably securable to the inner surface.

26. The garment of claim 23, wherein the pocket is sized and dimensioned to hold the second end region within the pocket.

27. The garment of claim 23, wherein the crotch portion includes a wicking material.

28. The garment of claim 23, wherein the garment includes a fluid absorption material.

29. The garment of claim 23, further comprising an additional strap partially defining a through hole between the additional strap and the inner surface, the through hole of the additional strap being sized and dimensioned to secure the conduit of the fluid collection device therein.

30. The garment of claim 23, further comprising one or more adjustable straps configured to alter a position of the crotch portion and the fluid collection device with respect to the urethra of the user.

31. The fluid collection system of claim 10, further comprising an additional strap secured to the inner surface of the garment and at least partially defining a through hole between the additional strap and the inner surface, wherein the additional strap is positioned on the crotch portion of the garment to receive a portion of the fluid impermeable barrier therethrough.

* * * * *